(12) United States Patent
Nikoonahad

(10) Patent No.: US 6,867,862 B2
(45) Date of Patent: Mar. 15, 2005

(54) SYSTEM AND METHOD FOR CHARACTERIZING THREE-DIMENSIONAL STRUCTURES

(75) Inventor: Mehrdad Nikoonahad, 271 Oakhurst Pl., Menlo Park, CA (US) 94025

(73) Assignee: Mehrdad Nikoonahad, Menlo Park, CA (US)

( * ) Notice: Subject to any disclaimer, the term of this patent is extended or adjusted under 35 U.S.C. 154(b) by 0 days.

(21) Appl. No.: 10/718,780

(22) Filed: Nov. 20, 2003

(65) Prior Publication Data

US 2004/0105099 A1 Jun. 3, 2004

Related U.S. Application Data

(60) Provisional application No. 60/427,762, filed on Nov. 20, 2002.

(51) Int. Cl.[7] .............................................. G01N 21/88
(52) U.S. Cl. ...................................... 356/340; 356/636
(58) Field of Search ................ 356/237.1, 237.2–237.5, 356/301, 335–343, 239.1–239.8, 630, 636

(56) References Cited

U.S. PATENT DOCUMENTS

| | | |
|---|---|---|
| 4,999,014 A | 3/1991 | Gold et al. |
| 5,042,951 A | 8/1991 | Gold et al. |
| 5,181,080 A | 1/1993 | Fanton et al. |
| 5,329,357 A | 7/1994 | Bernoux et al. |
| 5,412,473 A | 5/1995 | Rosencwaig et al. |
| 5,596,411 A | 1/1997 | Fanton et al. |
| 5,604,344 A | 2/1997 | Finarov et al. |
| 5,608,526 A | 3/1997 | Piwonka-Corle et al. |
| 5,747,813 A | 5/1998 | Norton et al. |
| 5,771,094 A | 6/1998 | Carter et al. |
| 5,867,276 A | * 2/1999 | McNeil et al. ............... 356/445 |
| 6,115,117 A | * 9/2000 | Isozaki ..................... 356/237.4 |
| 6,124,924 A | 9/2000 | Feldman et al. |

(List continued on next page.)

OTHER PUBLICATIONS

Logofatu, Petre C., "UV Scatterometry," Proceedings of SPIE: Metrology, Inspection, and Process Control for Microlithography XVII, May 2003, pp. 208–214, vol. 5038, The International Society for Optical Engineering (SPIE), Bellingham, Washington, USA.

(List continued on next page.)

*Primary Examiner*—Richard A. Rosenberger
*Assistant Examiner*—Vincent P. Barth

(57) ABSTRACT

A metrology system for characterizing three-dimensional structures and methods for manufacturing and using same. The metrology system includes a measurement system that preferably comprises an energy source and energy detector and that is in communication with a processing system. Under control of the processing system, the metrology system rotates the measurement system relative to a structure while the energy source directs a beam of incident energy toward the structure. The incident energy rebounds from the structure as scattered energy, at least a portion of which propagates toward the energy detector. Due to the relative rotation, the energy detector receives scattered energy from the structure at a plurality of angles, and the measurement system produces data signals therefrom, which data signals are provided to the processing system. The processing system analyzes the data signals to determine whether the structure has any defects, such as yield limiting deviations or other processing defects.

82 Claims, 19 Drawing Sheets

U.S. PATENT DOCUMENTS

| | | | |
|---|---|---|---|
| 6,323,946 B1 | 11/2001 | Norton | |
| 6,429,943 B1 | 8/2002 | Opsal et al. | |
| 6,433,878 B1 | 8/2002 | Niu et al. | |
| 6,451,621 B1 | 9/2002 | Rangarajan et al. | |
| 6,483,580 B1 | 11/2002 | Xu et al. | |
| 6,556,303 B1 * | 4/2003 | Rangarajan et al. | 356/446 |
| 6,583,731 B2 | 6/2003 | Chan et al. | |
| 6,608,686 B1 | 8/2003 | Lane et al. | |
| 6,608,690 B2 | 8/2003 | Niu et al. | |
| 6,633,831 B2 | 10/2003 | Nikoonahad et al. | |
| 6,636,843 B2 | 10/2003 | Doddi et al. | |
| 6,645,824 B1 | 11/2003 | Yang et al. | |
| 6,665,071 B2 | 12/2003 | Hovinen et al. | |
| 6,689,519 B2 | 2/2004 | Brown et al. | |
| 6,694,275 B1 | 2/2004 | Jakadar et al. | |
| 6,694,284 B1 | 2/2004 | Nikoonahad et al. | |
| 6,704,661 B1 | 3/2004 | Opsal et al. | |
| 6,721,052 B2 | 4/2004 | Zhao et al. | |
| 2002/0051564 A1 | 5/2002 | Benesch et al. | |
| 2002/0101585 A1 | 8/2002 | Benesch et al. | |
| 2003/0206298 A1 | 11/2003 | Bischoff et al. | |
| 2004/0017574 A1 | 1/2004 | Vuong et al. | |
| 2004/0070772 A1 | 4/2004 | Shchegrov et al. | |

OTHER PUBLICATIONS

Hettwer, Andrea et al., "Phi–Scatterometry for Integrated Linewidth and Process Control in DRAM Manufacturing," IEEE Transactions on Semiconductor Manufacturing, Nov. 2002, pp. 470–477, vol. 15, No. 4, Institute of Electrical and Electronics Engineers (IEEE), New York, New York, USA.

Niu, Xinhui et al., "Specular Spectroscopic Scatterometry," IEEE Transactions on Semiconductor Manufacturing, May 2001, pp. 97–111, vol. 14, No. 2, Institute of Electrical and Electronics Engineers (IEEE), New York, New York, USA.

Schneider, Claus et al., "Integrated metrology: An enabler for advanced process control (APC)," Proceedings of SPIE: In–Line Characterization, Yield, Reliability, and Failure Analysis in Microelectronic Manufacturing II, Apr. 2001, pp. 118–130, vol. 4406, The International Society for Optical Engineering (SPIE), Bellingham, Washington, USA.

Benesch, Norbert et al., "Phi–Scatterometry for Integrated Linewidth Control in DRAM Manufacturing," 2001 IEEE International Symposium on Semiconductor Manufacturing, Oct. 8–10, 2001, pp. 129–132, IEEE Catalog No. 01CH37203, San Jose, California, USA.

Coulombe, Stephen A. et al., "Scatterometry measurement of sub–0.1 $\mu$m linewidth gratings," Journal of Vacuum Science & Technology B: Microelectronics and Nanometer Structures, Jan., 1998, pp. 80–87, vol. 16, Issue 1, American Vacuum Society, Research Triangle Park, North Carolina, USA.

Raymond, Christopher J. et al., "Multiparameter grating metrology using optical scatterometry," Journal of Vacuum Science & Technology B: Microelectronics and Nanometer Structures, Mar., 1997, pp. 361–368, vol. 15, Issue 2, American Vacuum Society, Research Triangle Park, North Carolina, USA.

Giovannini, H. et al., "Angle–resolved polarimetric phase measurement for the characterization of gratings," Optics Letters, Oct. 15, 1996, pp. 1619–1621, vol. 21, No. 20, Optical Society of America, Washington, DC, USA.

* cited by examiner

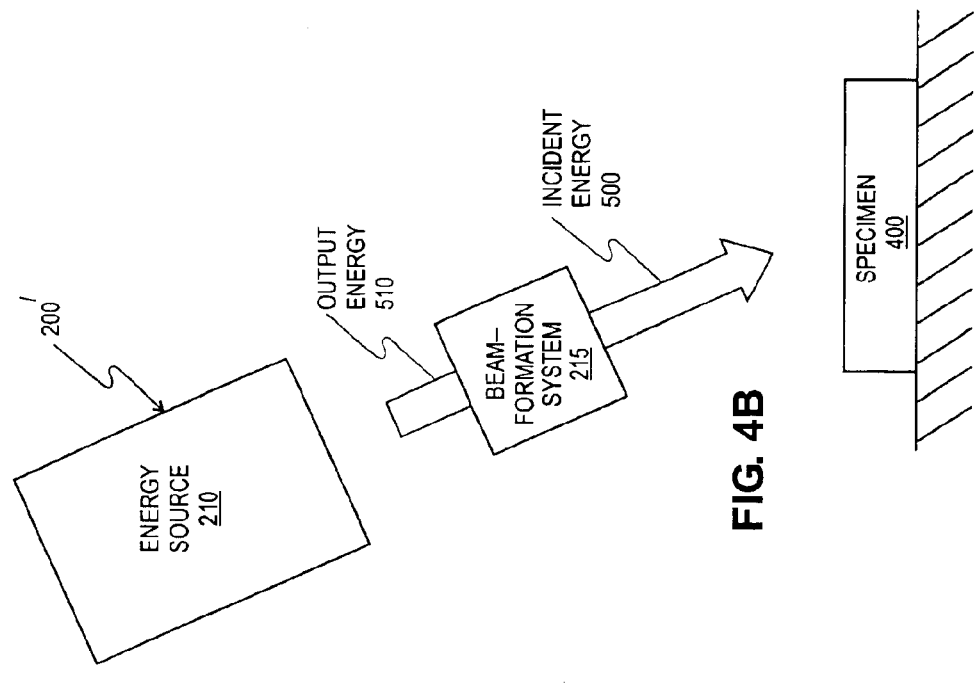
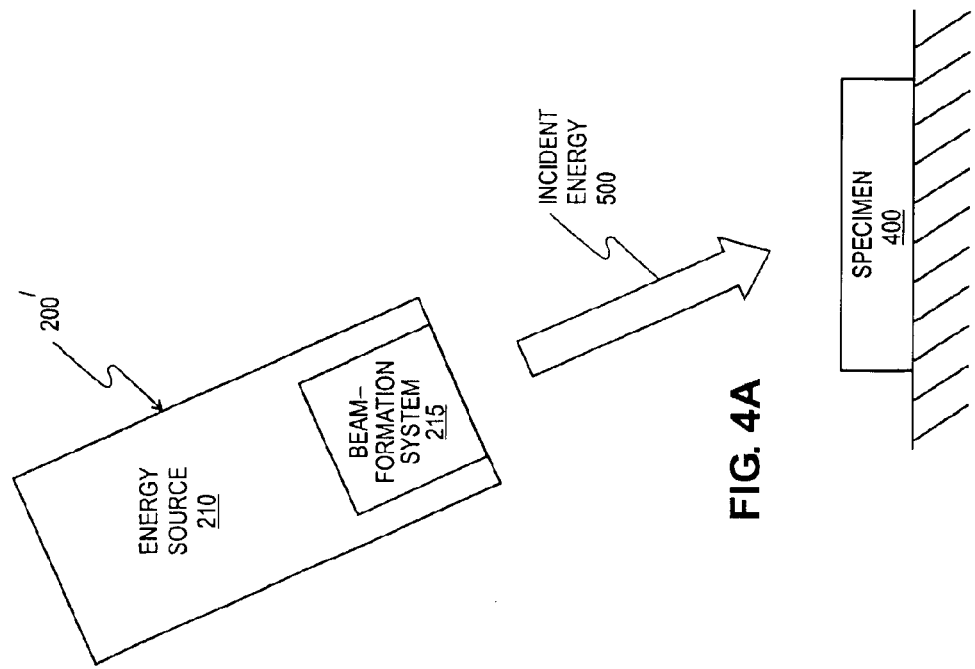

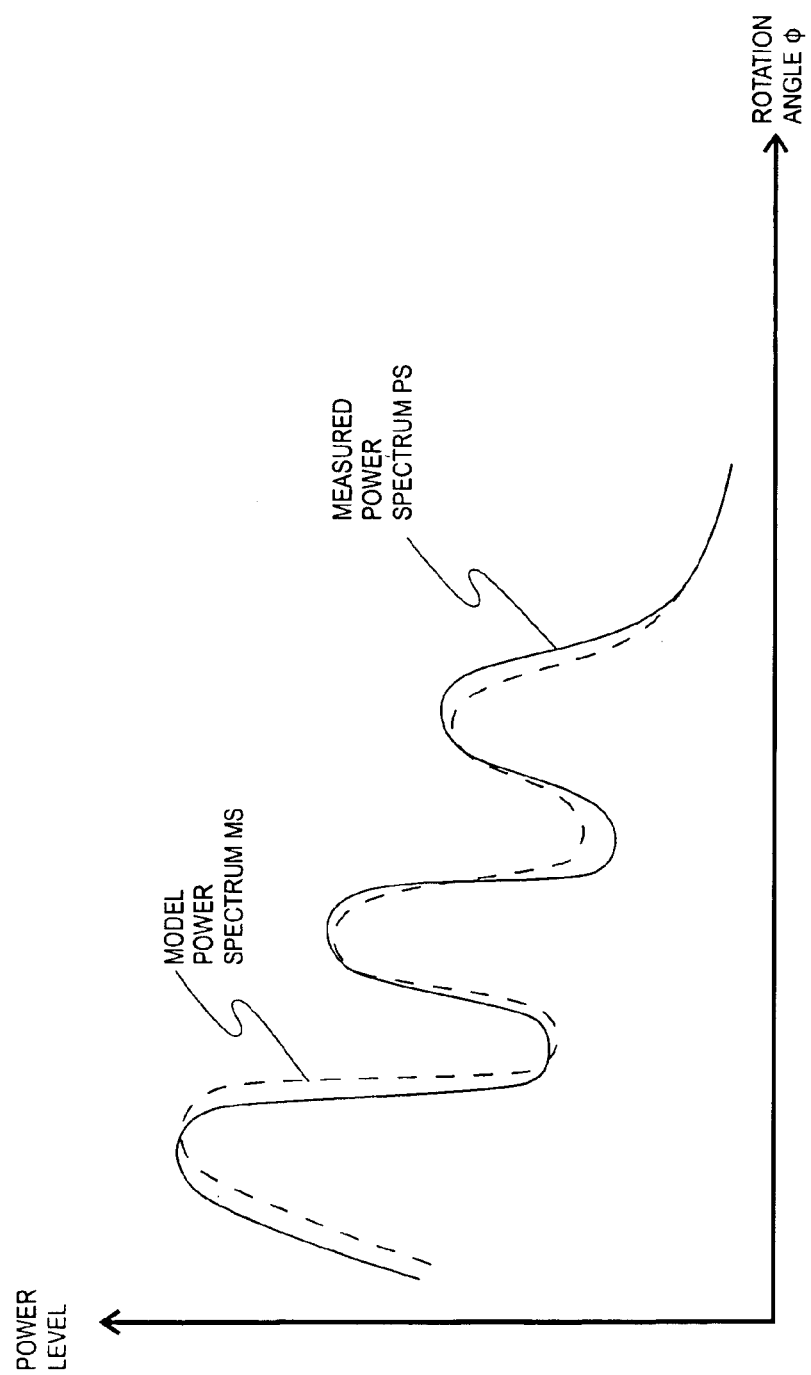

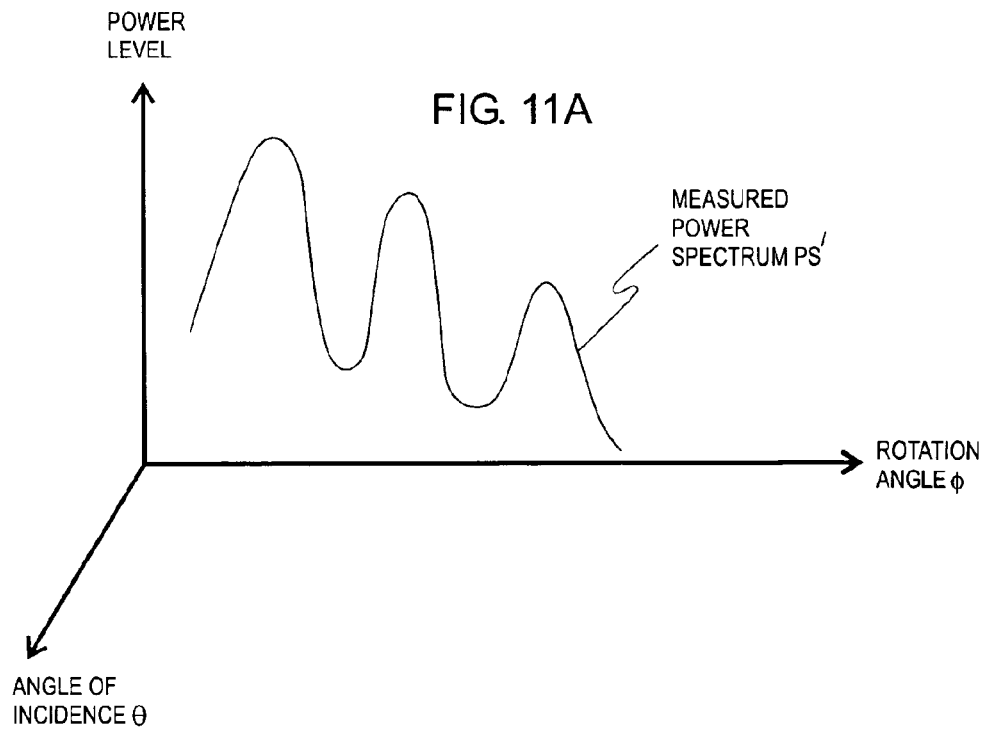
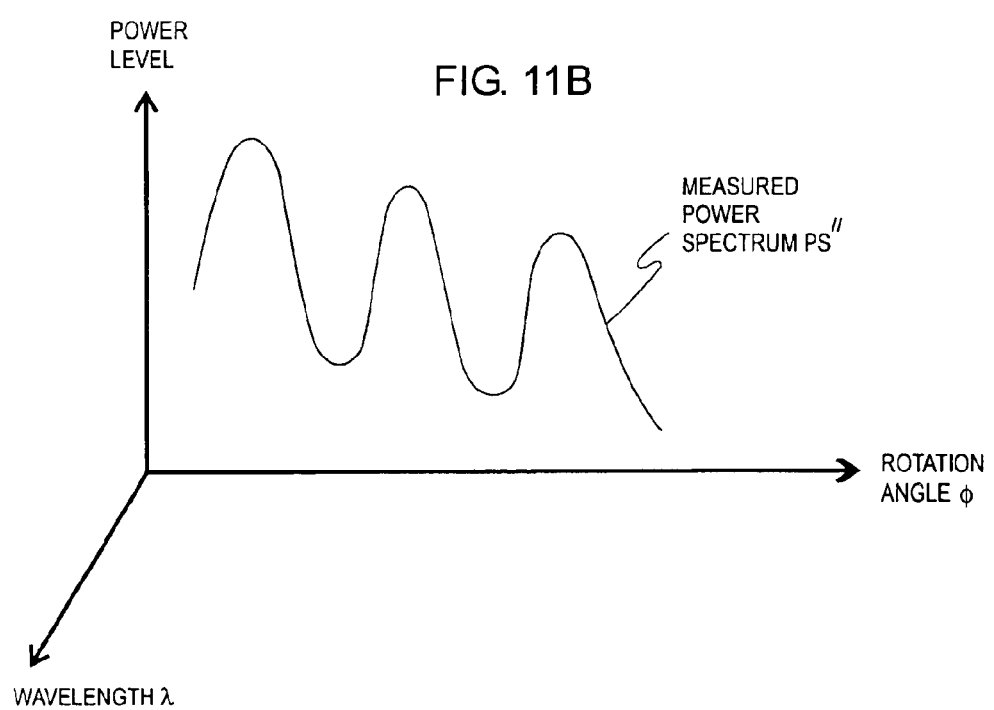

SYSTEM AND METHOD FOR CHARACTERIZING THREE-DIMENSIONAL STRUCTURES

CROSS-REFERENCE TO RELATED APPLICATIONS

This application claims priority to U.S. Provisional Application Ser. No. 60/427,762, entitled "System and Method for Characterization of Small Three Dimensional Structures," filed on Nov. 20, 2002. Priority to the prior provisional application is expressly claimed, and the disclosure of the provisional application is hereby incorporated by reference in its entirety.

FIELD OF THE INVENTION

The present invention relates generally to metrology and/or process monitoring systems and more particularly, but not exclusively, to optical metrology and/or process monitoring systems for characterizing yield limiting deviations and defects during semiconductor processing.

BACKGROUND OF THE INVENTION

Semiconductor processing is a well established technology for making microelectronic devices. This technology involves depositing thin films of insulator (dielectric) and metallic materials on the surface of semiconductor wafer. These films vary in thickness from a few Angstroms to a few microns depending on what function they serve in the structure of an electronic device. The device is built layer by layer starting from the surface of the semiconductor. The transistors, which are the active part of the device, are formed in the semiconductor and film stacks consisting of alternating metal-dielectric structures are built on top of the semiconductor. These thin films are etched at specific lithographically defined locations to form vias or contact holes. These vias or contacts are filled with conducting materials such as metals so that connections can be made from upper layer interconnects to lower layer interconnects. Interconnects connect different points of the device to each other within one plane.

There are tight tolerances for film thicknesses and lateral dimensions of the structures involved. Any deviation or excursion from a set of predefined design rules can be a serious yield limiting issue in the manufacturing of these devices. For example, if the thickness of a given layer deviates from the required specification, there would be a severe penalty on yield—a wrong film thickness is therefore a yield limiting deviation or defect. These issues have only become more important as integrated circuit processing technology advances to allow smaller device geometries. For this reason, film characterization has proven to be an important part of monitoring the yield and the operation of the device. Current technologies for film characterization include spectroscopic ellipsometry and reflectometry. Both these techniques rely on reflection of light from planar interfaces and they take advantage of changes in Fresnel reflectivity with wavelength and angle of illumination and their application to semiconductor processing is covered under U.S. Pat. Nos. 4,999,014; 5,042,951; 5,181,080; 5,329,357; 5,412,473; 5,596,411; 5,608,526; 5,771,094; 5,747,813; 5,917,594; and 6,323,946. It is important to note that for film characterization, reflectometry and ellipsometry rely on reflection of light from two-dimensional (2D) planes of film interfaces. Recently, a technology called scatterometry, covered under U.S. Pat. Nos. 6,429,943, 6,433,878, 6,483,580, 6,451,621 has emerged which can use the same hardware as an ellipsometer or a reflectometer for dimensional measurements. For example with these techniques the smallest dimension (critical dimension) printed, may be measured. As the world of microelectronics is moving toward nanotechnology, both critical dimension (CD) metrology and film thickness measurement are playing an increasingly vital role in high performance device fabrication. The devices of the future will require an increasing numbers of lithography masking steps, thereby increasing and accelerating the number of corresponding CD and film measurement steps.

Many structures, and their corresponding yield limiting deviations and defects are, in general, three-dimensional (3D). This is true for both the at the transistor level and also at the subsequent metal layers. At the transistor level one would be interested in measuring the sidewall angle, height, and profile of a feature with minimum dimensions. A wrong CD, profile, or sidewall angle would also be a yield limiting deviation or defect.

For interconnects, recently, the copper Damascene process has become the preferred technology. In this technology a layer of diffusion barrier material such as TaN is deposited on the walls of the trench and via. This process step is followed by depositing a seed layer of copper on top of the barrier layer. And finally through electroplating a thicker layer of copper fills up the trenches and vias. This process then is followed by the Chemical Mechanical Planarization (CMP). FIGS. 1A–B show the top and side views, respectively, of this structure after CMP. FIG. 1A shows the copper lines, the diffusion barrier layer and the inter-metal dielectric (IMD) layer separating the conductor lines from each other. In FIG. 1B, the side view additionally shows the trench etch stop, interlayer dielectric (ILD) and the dielectric diffusion barrier and the via for making connection to the lower layer. In FIG. 1C, some of the problems associated with the copper Damascene are captured and some typical thicknesses for the films involved are given. Firstly, the dishing and erosion of the copper is shown. Since copper is a soft material during CMP, the material loses planarity and the surface becomes bowed. This can make lithography of the subsequent steps complicated and can lead to a reduction in yield.

The side wall coverage with the barrier material is another major problem. This is because vacuum deposition, while effective on flat surfaces, can be problematic when it comes to high aspect ratio trenches and vias. Proper coverage of the sidewalls with the barrier material can cause the diffusion of the copper and can lead to serious problems, ultimately limiting the fabrication yield. Formation of voids within the copper is another major problem that arises during the electroplating process. Voids such as the one shown in FIG. 2 increase the electrical resistance of the trench and via and can lead to high current densities and heating. As is clear, these problems usually are in three dimensions. Prior art ellipsometry and reflectometry fail to characterize such yield limiting deviations. Therefore, a need clearly exists for characterizing these three-dimensional deviations in conjunction with film characterization and film thickness measurement.

In view of the foregoing, a need exists for an improved metrology and/or process monitoring system that overcomes the aforementioned obstacles and deficiencies of currently-available systems.

SUMMARY OF THE INVENTION

The various embodiments disclosed herein are directed toward a metrology and/or process monitoring system (herein referred to, separately and collectively, as a "metrology system") that is configured to characterize three-dimensional structures to determine whether the structures have any defects, such as yield limiting deviations or other processing defects.

Each of the embodiments comprises a metrology system including a measurement system that is in communication with a processing system. Being configured to characterize a three-dimensional structure formed on a specimen, the metrology system can rotate the measurement system relative to the specimen while the measurement system directs a beam of incident energy toward the specimen. The rotation of the measurement system relative to the specimen is performed along an axis of rotation that preferably is substantially perpendicular to a surface of the specimen and intersects the structure. Propagating toward the specimen substantially at an angle of illumination relative to the axis of rotation, the incident energy rebounds from the specimen as scattered energy, at least a portion of which propagates toward the measurement system.

The measurement system also is configured to receive the scattered energy and to produce data signals therefrom, providing the data signals to the processing system. As the relative rotation continues, the measurement system receives scattered energy associated with each of a plurality of rotation angles and produces additional data signals, which likewise are provided to the processing system. Thereby, a spectrum of data signals is produced with respect to the plurality of rotation angles. Receiving the spectrum of data signals from the measurement system, the processing system is configured to perform an analysis of the data signals to determine whether the structure has any defects, such as yield limiting deviations or other processing defects.

Other aspects and features of the various embodiments disclosed herein will become apparent from consideration of the following description taken in conjunction with the accompanying drawings.

BRIEF DESCRIPTION OF THE DRAWINGS

FIG. 4A is a detail drawing illustrating one embodiment of an energy source for the measurement system of FIG. 3.

FIG. 4B is a detail drawing illustrating an alternative embodiment of the energy source of FIG. 4A.

FIG. 10 illustrates an exemplary two-dimensional power spectrum characterization of the structure of FIG. 9.

FIGS. 11A–B illustrate exemplary three-dimensional power spectrum characterizations of the structure of FIG. 9.

Figure 1A:
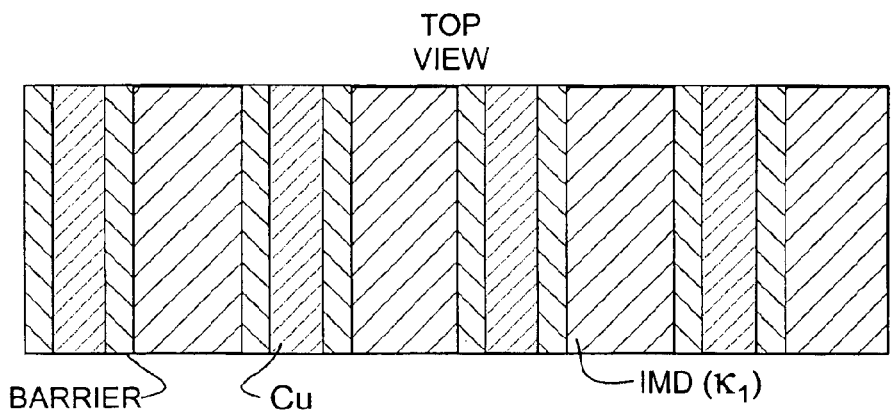
FIG. 1A is a top view of a prior art Copper Damascene structure after a Chemical Mechanical Planarization (CMP) process.
Figure 1B:
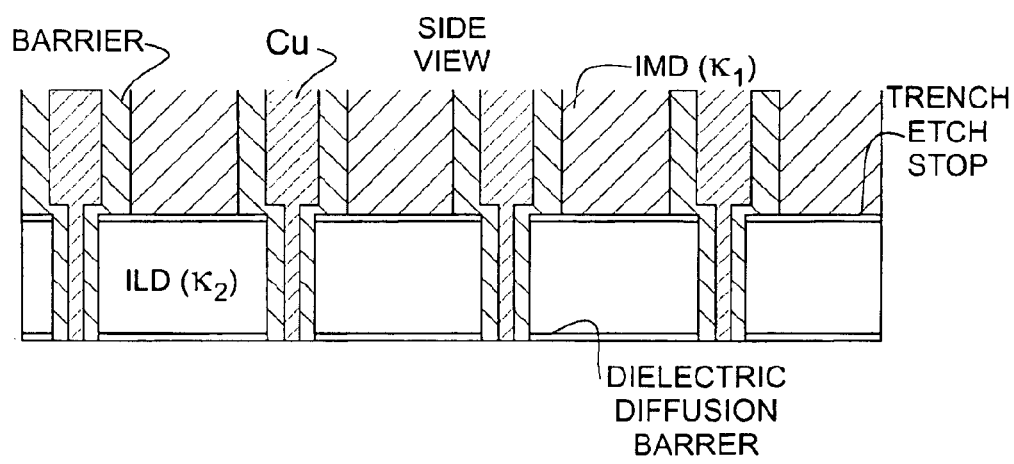
FIG. 1B is a side view of the prior art Copper Damascene structure of FIG. 1A.
Figure 1C:
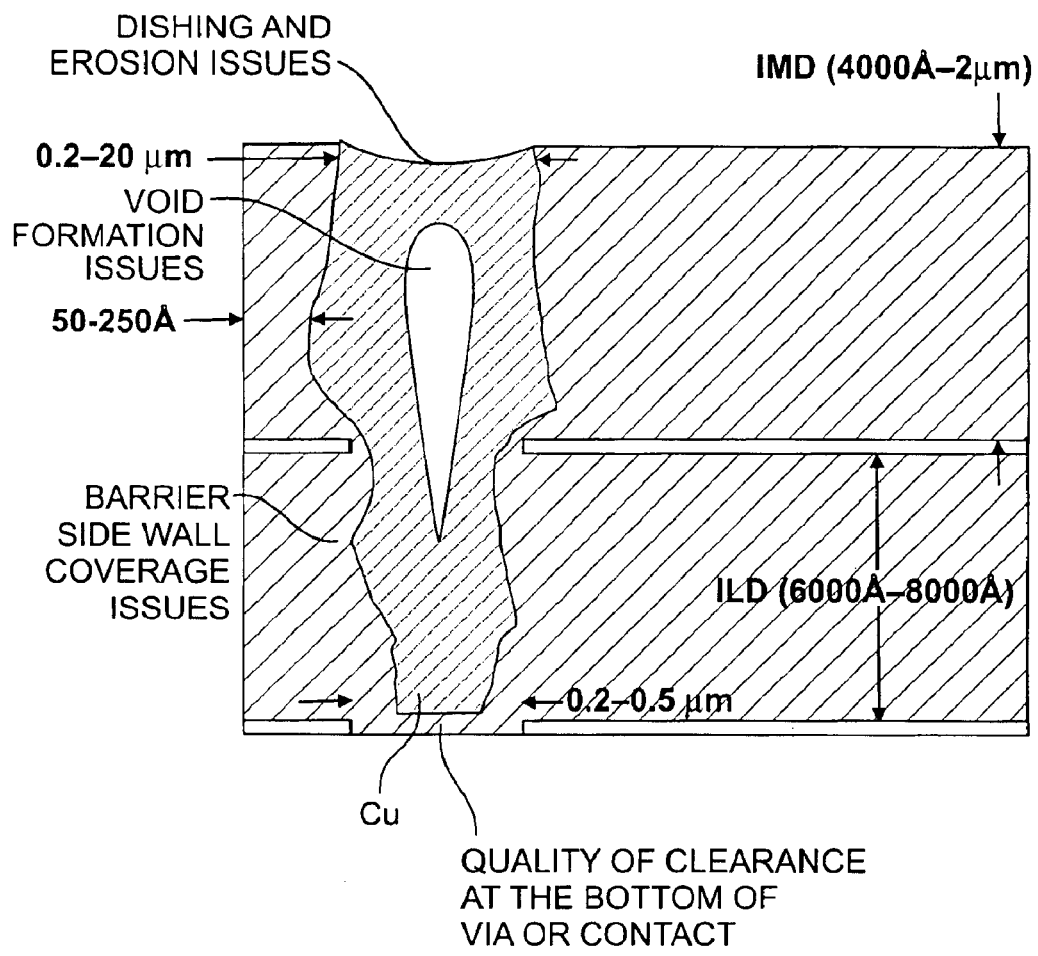
FIG. 1C illustrates typical problems associated with prior art Copper Damascene structures.

It should be noted that the figures are not drawn to scale and that elements of similar structures or functions are generally represented by like reference numerals for illustrative purposes throughout the figures. It also should be noted that the figures are only intended to facilitate the description of the preferred embodiments of the present invention. The figures do not describe every aspect of the present invention and do not limit the scope of the invention.

DETAILED DESCRIPTION OF THE PREFERRED EMBODIMENTS

Figure 2:
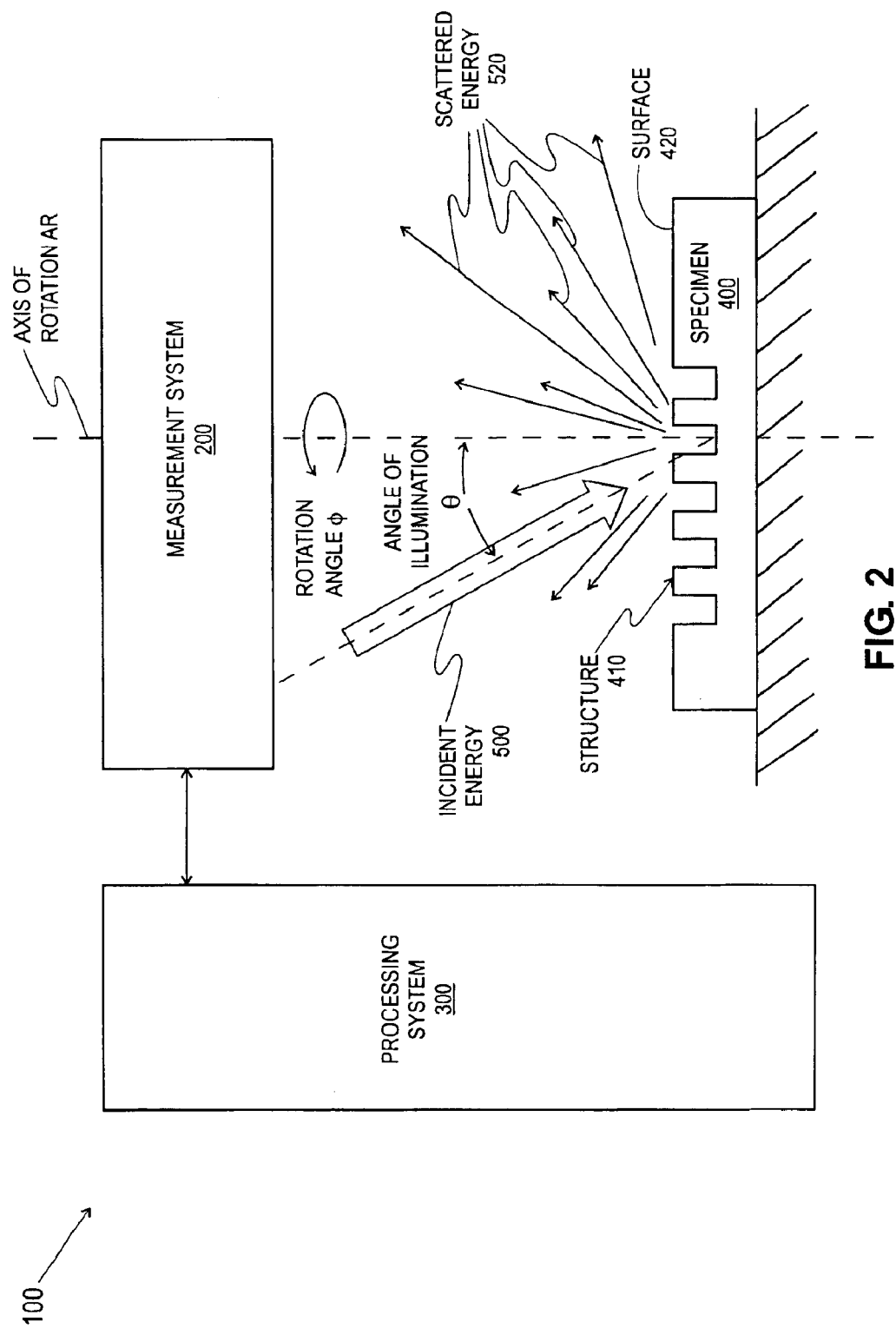
FIG. 2 is an exemplary block diagram of an embodiment of a metrology and/or process monitoring system ("metrology system") for characterizing three dimensional structures.

Since current metrology and/or process monitoring systems (herein referred to, separately and collectively, as "metrology systems") are inadequate for complex structures, can be destructive, and can prove difficult and costly to implement, a metrology system for characterizing three dimensional structures that is configured to rotate relative to the three dimensional structures during characterization can prove much more desirable and provide a basis for a wide range of industrial applications, such as the characterization of yield limiting deviations and defects during semiconductor processing. This result can be achieved, according to one embodiment disclosed herein, by employing a metrology system 100 as shown in FIG. 2.

The exemplary metrology system 100 includes a measurement system 200 that is coupled with, and configured to communicate with, a processing system 300. Being configured to characterize a three-dimensional structure 410 formed on a specimen 400, the metrology system 100 can rotate the measurement system 200 relative to the specimen 400 while the measurement system 200 directs a beam of incident energy 500 toward the specimen 400. As illustrated in FIG. 2, the rotation of the measurement system 200 relative to specimen 400 is performed along an axis of rotation AR that preferably is substantially perpendicular to an external surface 420 of the specimen 400 and intersects the structure 410. Propagating toward the specimen 400 substantially at an angle of illumination (or angle of incidence) θ relative to the axis of rotation AR, the incident energy 500 rebounds from the specimen 400 as scattered energy 520. The scattered energy 520 rebounds from the specimen 400 in a plurality of directions as illustrated in FIG. 2. At least a portion of the scattered energy 520 propagates toward the measurement system 200.

The measurement system 200 also is configured to receive the portion of the scattered energy 520 and to produce data signals (not shown) therefrom, providing the data signals to the processing system 300. As the relative rotation continues, the measurement system 200 receives scattered energy 520 associated with each of a plurality of rotation angles (or azimuthal angles) φ and produces additional data signals, which likewise are provided to the processing system 300. Thereby, a spectrum of data signals is produced with respect to the rotation angle φ. Receiving the spectrum of data signals, in whole or in part, from the measurement system 200, the processing system 300 is configured to perform an analysis of the data signals to determine whether the structure 410 has any defects, such as yield limiting deviations or other processing defects. The processing system 300 can analyze the data signals in any suitable manner, such as by comparing the data signals with one or more mathematical models (not shown) of the structure 410 and/or by using a neural network that has been trained to identify structural defects.

Figure 3:
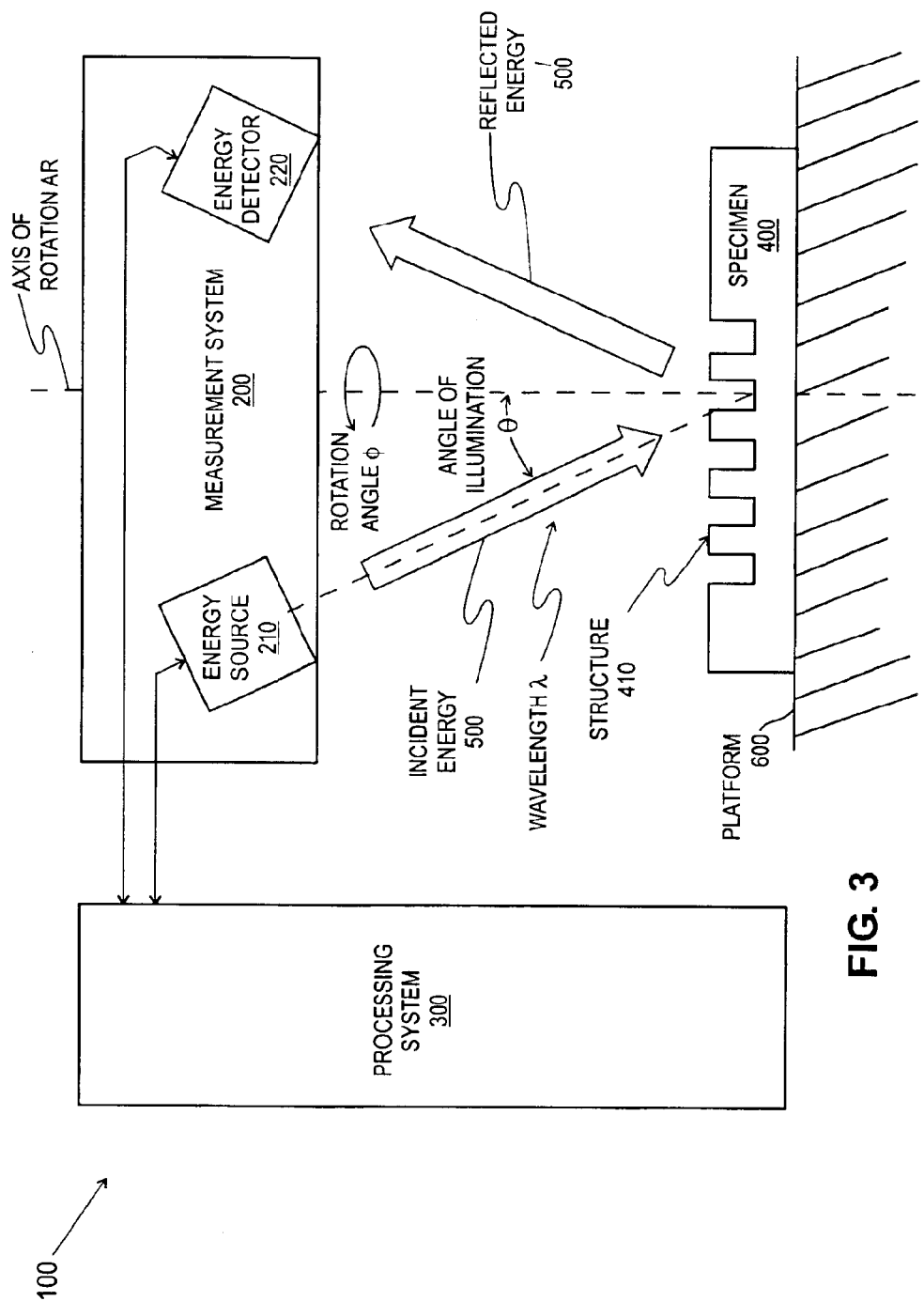
FIG. 3 is an exemplary block diagram illustrating one embodiment of a measurement system for the metrology system of FIG. 2.

Turning to FIG. 3, the metrology system 100 is shown as having a measurement system 200' that comprises an energy source 210 and an energy detector 220. Typically being coupled and preferably being substantially fixedly coupled, the energy source 210 and the energy detector 220 are approximately uniformly disposed about, and substantially in axial alignment with, the axis of rotation AR. Thereby, the energy source 210 and the energy detector 220 are configured to rotate substantially as a unit around the axis of rotation AR relative to the specimen 400.

As will be discussed in more detail below with reference to FIGS. 6A–B, the energy source 210 and the energy detector 220 can be provided in any appropriate configuration such that the energy detector 220 is configured to receive the scattered energy 520 (shown in FIG. 2). The suitability of a particular configuration may depend, at least in part, upon the nature of the specific application for which the metrology system 100 is to be utilized. Illustrative factors for identifying suitable configurations include the dimensions and complexity of the structure 410 being characterized, the materials from which the structure 410 is formed, and the desired precision of the characterization results. The measurement system 200' as shown in FIG. 3 is provided in the manner discussed in more detail below with reference to FIG. 6B and is configured to receive the incident energy 500 that reflects from the specimen 400 as reflected energy 500'.

The energy source 210 can be any type of energy source that can provide a suitable beam of incident energy 500, which preferably comprises electromagnetic radiation. Illustrative energy sources include monochromatic light sources, such as a gas laser or a solid state laser diode, and broadband sources, such as a xenon-arc lamp, as well as x-ray, ultraviolet, infra-red, and/or microwave energy. Being configured to direct the beam of incident energy 500 toward the specimen 400 in the manner discussed above with reference to the measurement system 200 (shown in FIG. 2), the energy source 210 can be coupled with, and can communicate with, the processing system 300 as illustrated in FIG. 3. The processing system 300, for example, can be configured to activate and deactivate the energy source 210 and/or to control the angle of illumination θ relative to the axis of rotation AR. The angle of illumination θ can comprise any suitable angle for directing the incident energy 500 toward the specimen 400. Therefore, the angle of illumination θ can be a substantially-fixed predetermined angle or can be adjustable among a plurality of predetermined angles within a predetermined range of angles.

Similarly, the processing system 300 can control a predetermined wavelength λ of the incident energy 500 provided by the energy source 210. The incident energy 500 has at least one predetermined wavelength λ that preferably is substantially within a predetermined range of wavelengths. Stated somewhat differently, the wavelength λ of the incident energy 500 can comprise a substantially-fixed predetermined wavelength or can vary among a plurality of predetermined wavelengths, such as a sweep of successive wavelengths, each being substantially within the predetermined range. The incident energy 500 also can be polychromatic energy, such as white light, simultaneously comprising a plurality of wavelengths λ. Although the incident energy 500 generally is shown and described herein as comprising optical waves and/or microwaves for purposes of illustration, it is understood that the wavelength λ of the incident energy 500 can be any suitable wavelength within any predetermined range and is not limited to the illustrated embodiments.

For example, the incident energy 500 can comprise radio waves having a frequency of up to approximately three gigahertz (<3 GHz) or microwaves having a frequency in a range substantially between three hundred megahertz and three hundred gigahertz (300 MHz–300 GHz). Likewise, the frequency of the incident energy 500 can be substantially within the infrared band having a wavelength between approximately seven hundred nanometers and one hundred micrometers (700 nm–100 μm), the visible band having a wavelength between approximately four hundred and seven hundred nanometers (400 nm–700 nm), the ultraviolet band having a wavelength between approximately four and four hundred nanometers (4 nm–400 nm), or the soft or hard x-ray band having a wavelength between approximately one picometer and ten nanometers (1 pm–10 nm). The selection of the predetermined wavelength λ and/or the predetermined range may depend, at least in part, upon the nature of the specific application for which the metrology system 100 is to be utilized in the manner discussed above. If comprising polychromatic light energy, the incident energy 500 can have a plurality of wavelengths λ within a range of between approximately one hundred and ninety nanometers and one and one-half microns (190 nm–1.5 microns), or a portion thereof, simultaneously.

It will be appreciated that the energy source 210 can include a beam-formation system (or beam-conditioning system) 215 as shown in FIGS. 4A–B. Being disposed substantially between the energy source 210 and the specimen 400, the beam-formation system 215 is configured to receive output energy 510 (shown in FIG. 4B) from the energy source 210 and to convert the output energy 510 into the beam of incident energy 500. As illustrated in FIG. 14B, for example, the beam-formation system 215 can include one or more polarization systems 215A, beam-splitting systems 215B, modulation systems 215C, 215G, mirrors 215D, 215F, wave plates 215E, beam-combining systems 215H, and/or any other suitable components. Exemplary modulation systems include phase or intensity modulation systems, such as an acousto-optic modulation (AOM) system. The beam-formation system 215 can be disposed substantially within the energy source 210 as illustrated in FIG. 4A or can be separate from the energy source 210 as shown in FIG. 4B.

Figure 5B:
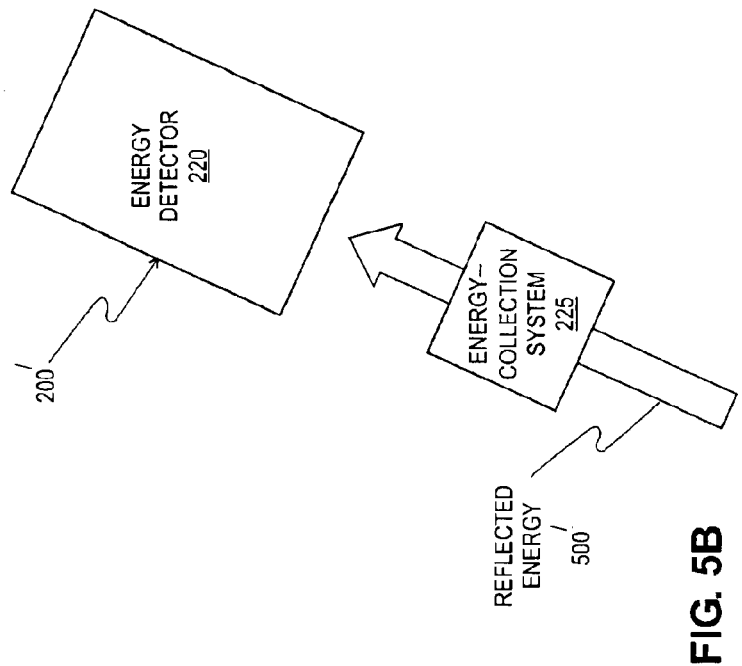
FIG. 5B is a detail drawing illustrating an alternative embodiment of the energy detector of FIG. 5A.
Figure 5A:
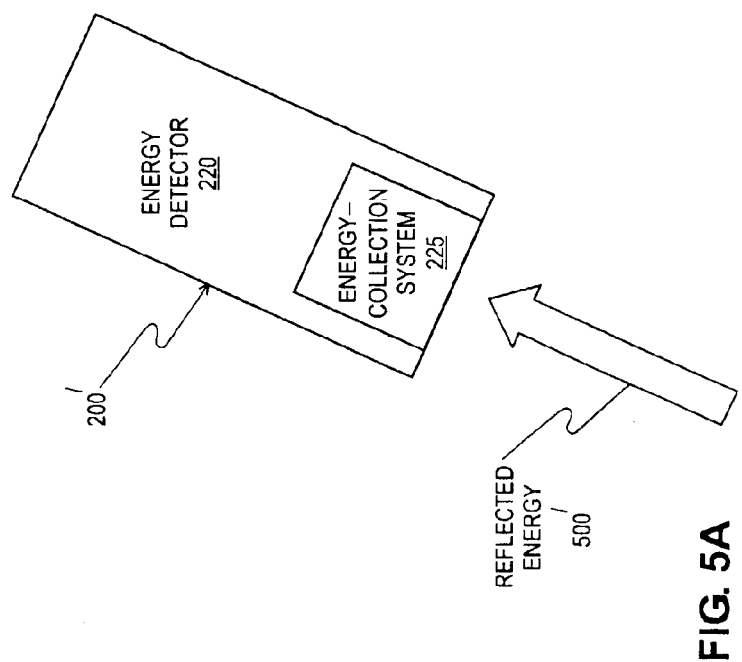
FIG. 5A is a detail drawing illustrating one embodiment of an energy detector for the measurement system of FIG. 3.

FIGS. 5A–B illustrate the energy detector 220 for the measurement system 200' (shown in FIG. 3). The energy detector 220 can comprise any type of energy detector that is suitable for detecting and/or receiving the reflected energy 500'. If the energy source 210 is a laser or light emitting diode system, for example, one or more photomultiplier tubes (PMT) and/or photodiodes can be used as the energy detector 220. Likewise, the energy detector 220 can comprise a wavelength dispersive element, such as a prism or grating, and a charge-coupled device (CCD) or photodiode array when the energy source 210 is a broadband or polychromatic source. Furthermore, the energy detector 220 can include one or more polarization elements, such as a polarization system 215A (shown in FIG. 14B) and/or a wave plate 215E (shown in FIG. 14B). The energy detector 220 likewise can comprise demodulator circuitry after the reflected energy 500' has been detected. The energy detector 220 also is coupled with, and can communicate with, the processing system 300. For example, preferably being configured to produce data signals from the reflected energy 500', the energy detector 220 configured to provide the data signals to the processing system 300 in the manner discussed above with regard to the measurement system 200 (shown in FIG. 2).

As desired, an energy-collection system (or collection system) 225 can be disposed substantially between the specimen 400 and the energy detector 220 as illustrated in FIGS. 5A–B. The energy-collection system 225 is configured to receive the reflections of the incident energy 500 from the specimen 400 and to convert these reflections into the reflected energy 500'. In the manner discussed above with regard to the beam-formation system 215 (shown in FIGS. 4A–B), the energy-collection system 225 can include any number of additional systems such as one or more polarization systems 215A (shown in FIG. 14B) and/or wave plates 215E (shown in FIG. 14B). As shown in FIG. 5A, the energy-collection system 225 can be disposed substantially within the energy detector 220, or the energy-collection system 225 can be separate from the energy detector 220 as shown in FIG. 5B.

Figure 6A:
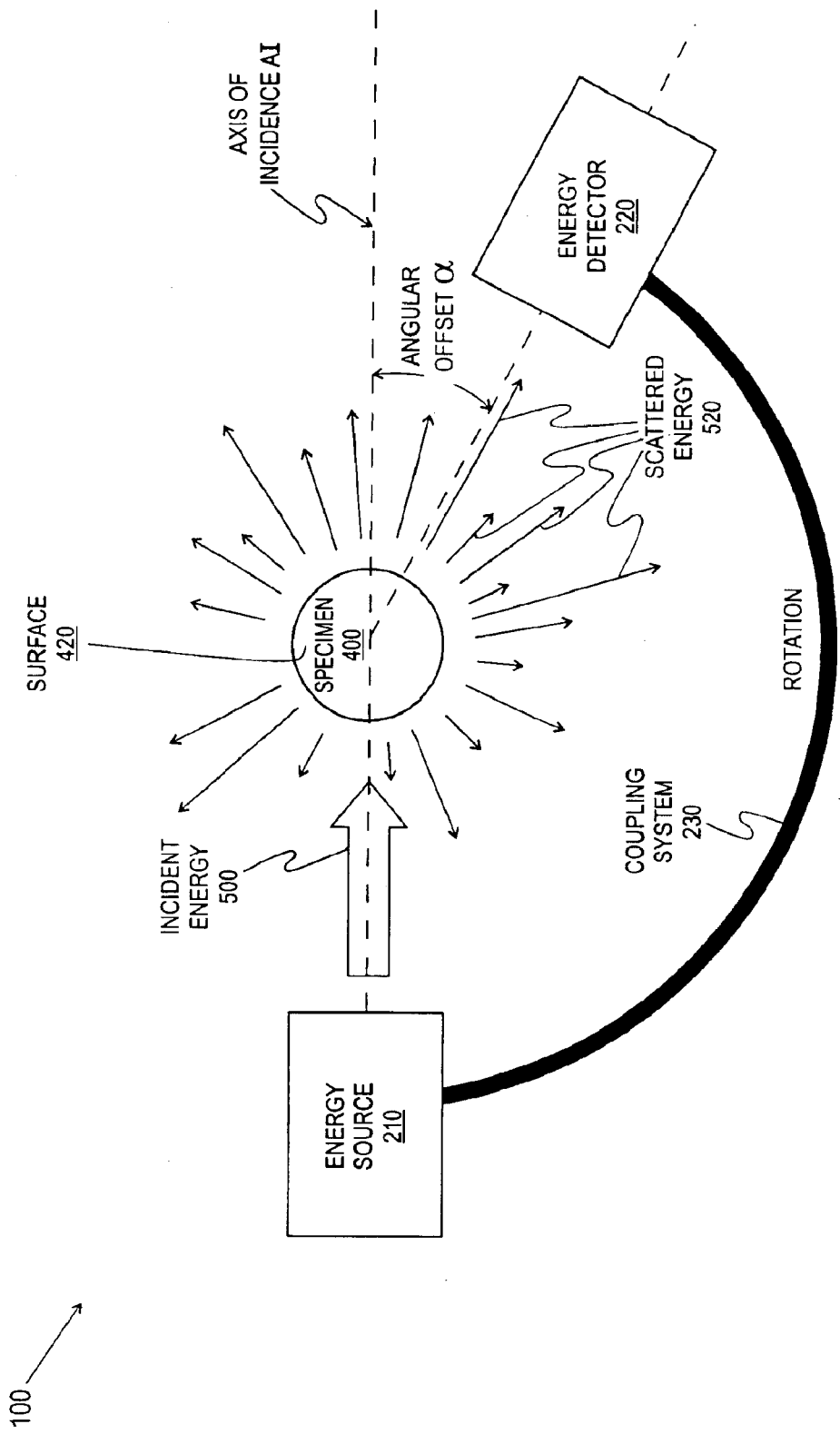
FIG. 6A is a top view of the metrology system of FIG. 3 and illustrates a dark field detection configuration of the energy source of FIGS. 4A–B and the energy detector of FIGS. 5A–B.
Figure 6B:
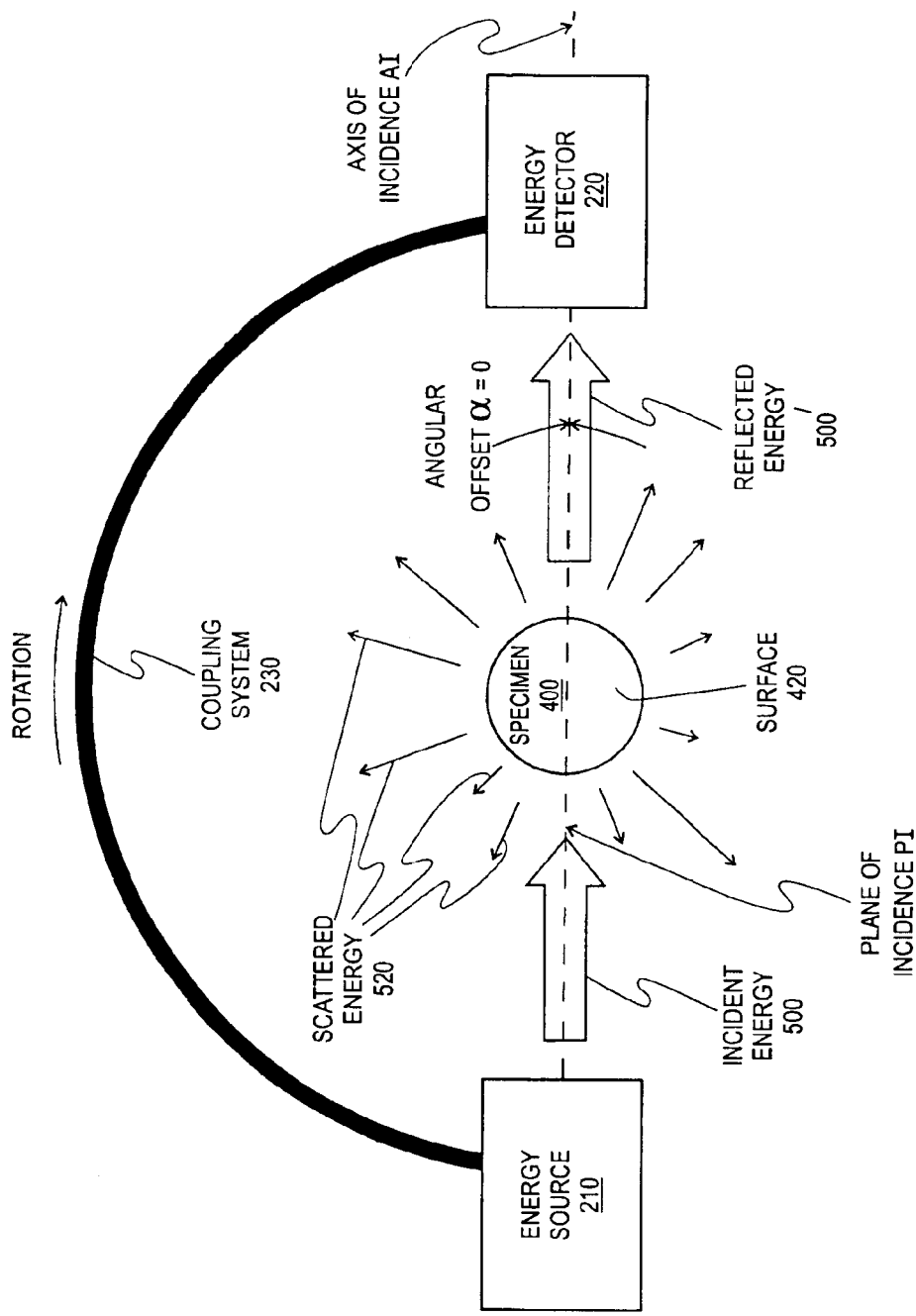
FIG. 6B is a top view of the metrology system of FIG. 3 and illustrates a bright field detection configuration of the energy source of FIGS. 4A–B and the energy detector of FIGS. 5A–B.

One configuration of the energy source 210 and the energy detector 220 of the measurement system 200' (shown in FIG. 3) is shown in FIGS. 6A–B. As illustrated in FIG. 6A, the beam of incident energy 500 propagates from the energy source 210, defining an axis of incidence AI. The energy detector 220 can be displaced from the axis of incidence AI by an angular offset α. By being displaced from the axis of incidence AI by the angular offset α, the energy detector 220 is configured to detect and/or receive non-specular scatterings of the incident energy 500 from the specimen 400 as the scattered energy 520. It will be appreciated that the angular offset α can comprise any suitable angular offset and preferably is selected to enhance the sensitivity of the metrology system 100 to one or more preselected features, such as the structure 410 (shown in FIGS. 2 and 3) of the specimen 400 to be characterized. This configuration sometimes is referred to as a dark field detection configuration.

It will be appreciated that, if the surface 420 of the specimen 400 is substantially smooth, no significant dark field scattering with result from the reflection of the incident energy 500 from the surface 420. As such, when the measurement system 200' is provided in the dark field detection configuration, the scattered energy 520 primarily comprises energy scattered from the three-dimensional structure 410 formed on the specimen 400. The structure 410 therefore can be characterized by the scattered energy 520 rebounded from the structure 410, and any defects in the structure 410 can be detected.

When the angular offset α is substantially equal to zero, the energy detector 220 is substantially in axial alignment with the axis of incidence AI. In contrast to the dark field detection configuration of the measurement system 200', the energy detector 220 is configured to detect and/or receive specular scattering or reflection of the incident energy 500 from the specimen 400 as the reflected energy 500'. This configuration may be referred to as a bright field detection configuration and is illustrated in FIG. 6B. The energy source 210 and the energy detector 220 preferably are substantially fixedly coupled such that the angular offset α is approximately maintained during the rotation of the measurement system 200' relative to the specimen 400. As illustrated in FIGS. 6B, the energy source 210 and the energy detector 220 are substantially fixedly coupled via a coupling system 230, which can comprise any type of mechanical coupling system, including one or more brackets and/or platforms, such as the rotatable platform 710 shown in FIG. 7B.

Figure 8:
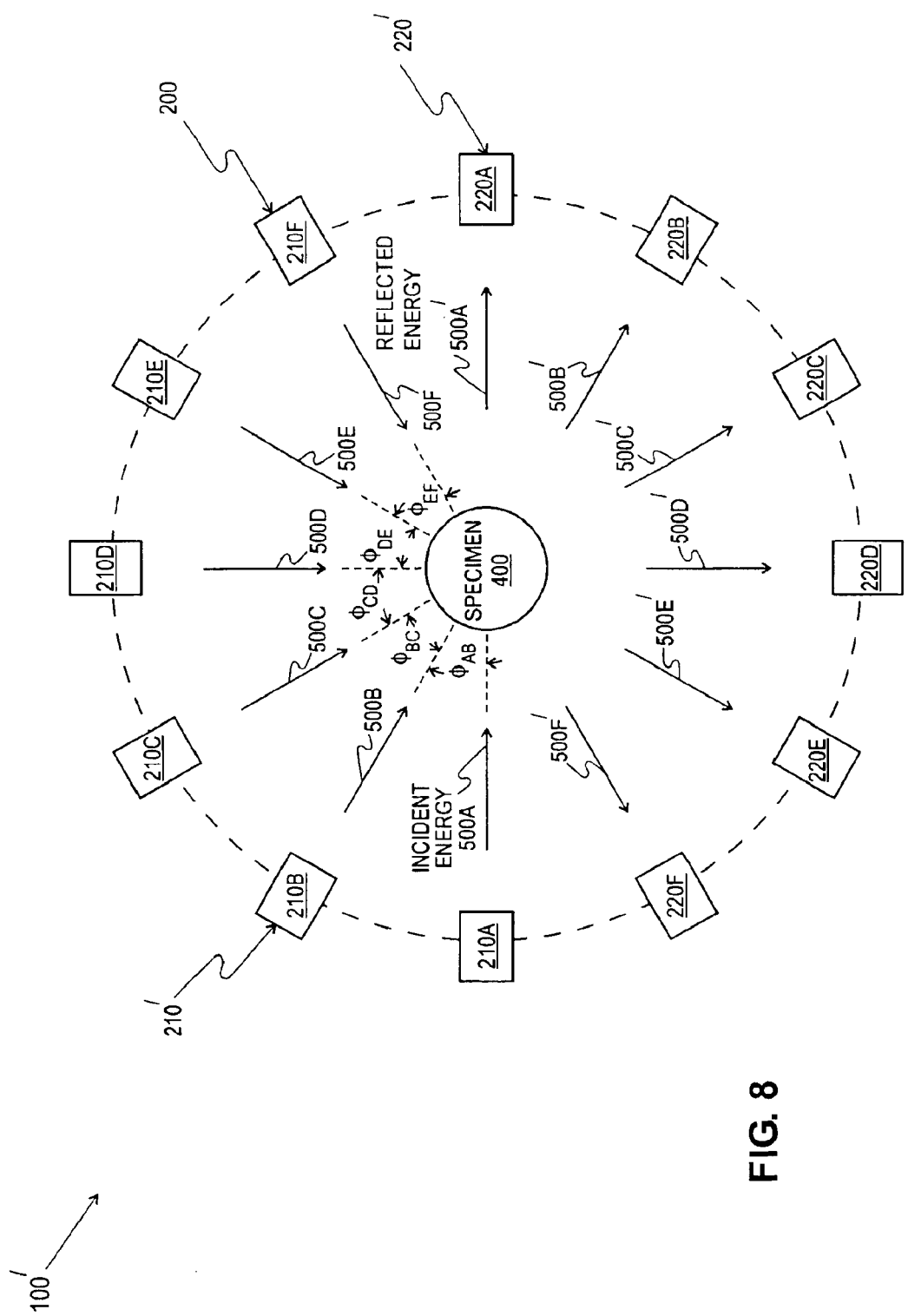
FIG. 8 is an exemplary block diagram illustrating an alternative embodiment of the measurement system of FIG. 3.
Figure 9:
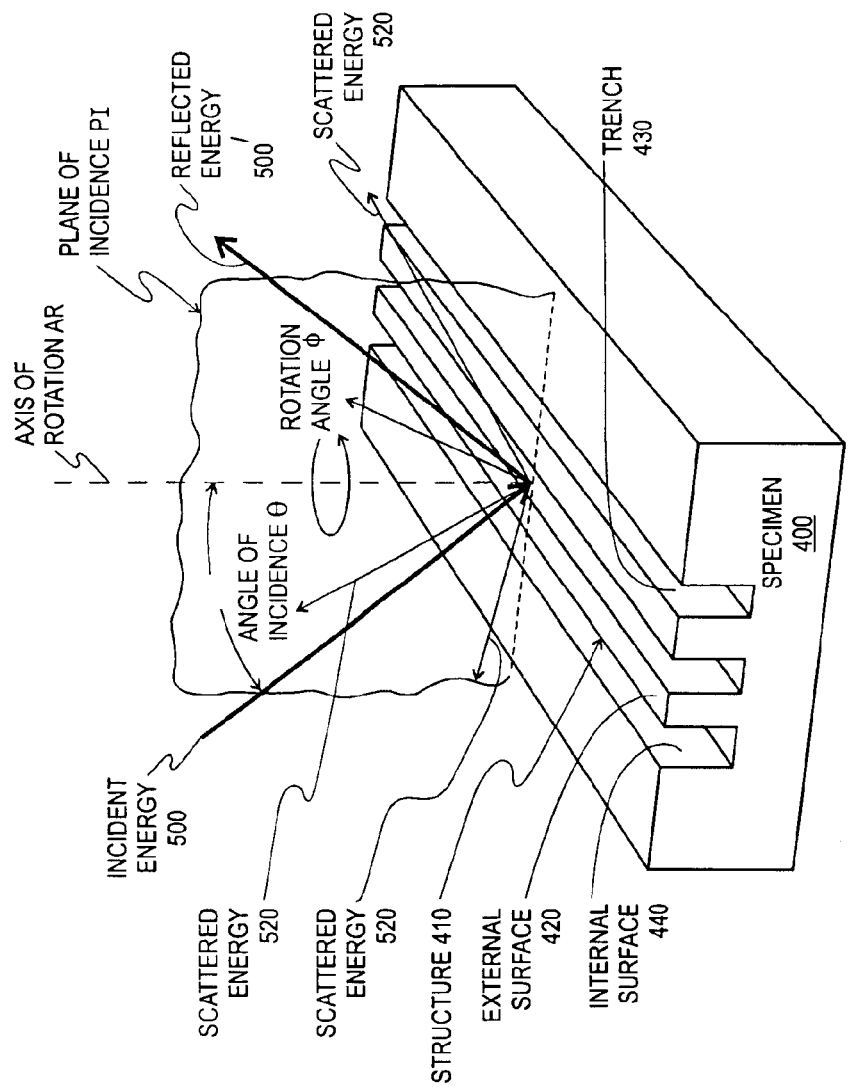
FIG. 9 is an exemplary three-dimensional structure for illustrating the operation of the metrology system of FIG. 2.

Since the energy source 210 and the energy detector 220 are substantially axially aligned, the incident energy 500 from the energy source 210 and the reflected energy 500' received by the energy detector 220 define a plane of incidence PI as shown in FIGS. 6B and 8. Since the axis of rotation AR preferably is substantially perpendicular to the surface 420 of the specimen 400, the plane of incidence PI likewise preferably is substantially perpendicular to the surface 420 as illustrated in FIG. 9. Therefore, when the energy source 210 and the energy detector 220 rotate about the axis of rotation AR (shown in FIG. 9), the plane of incidence PI likewise rotates about the axis of rotation AR.

Further, the phase of the incident energy 500 can be measured when the energy source 210 and the energy detector 220 are in the bright field detection configuration. For example, the metrology system 100 can include one or more beam-splitting systems 215B (shown in FIG. 14B) and/or beam-combining systems 215H (shown in FIG. 14B) for branching off a portion of the incident energy 500 to form a reference beam of incident energy (not shown). The reference beam can be directed toward the energy detector 220 such that the reference beam interferes with the reflected energy 500' Similarly, when the reflected energy 500' includes at least two components, such as a S-polarized component and a P-polarized component, the components of the reflected energy 500' can be interfered to provide a phase difference between the two components. It is understood that, as desired, the metrology system 100 can include a second energy source (not shown) that is configured to provide the reference beam.

Figure 7A:
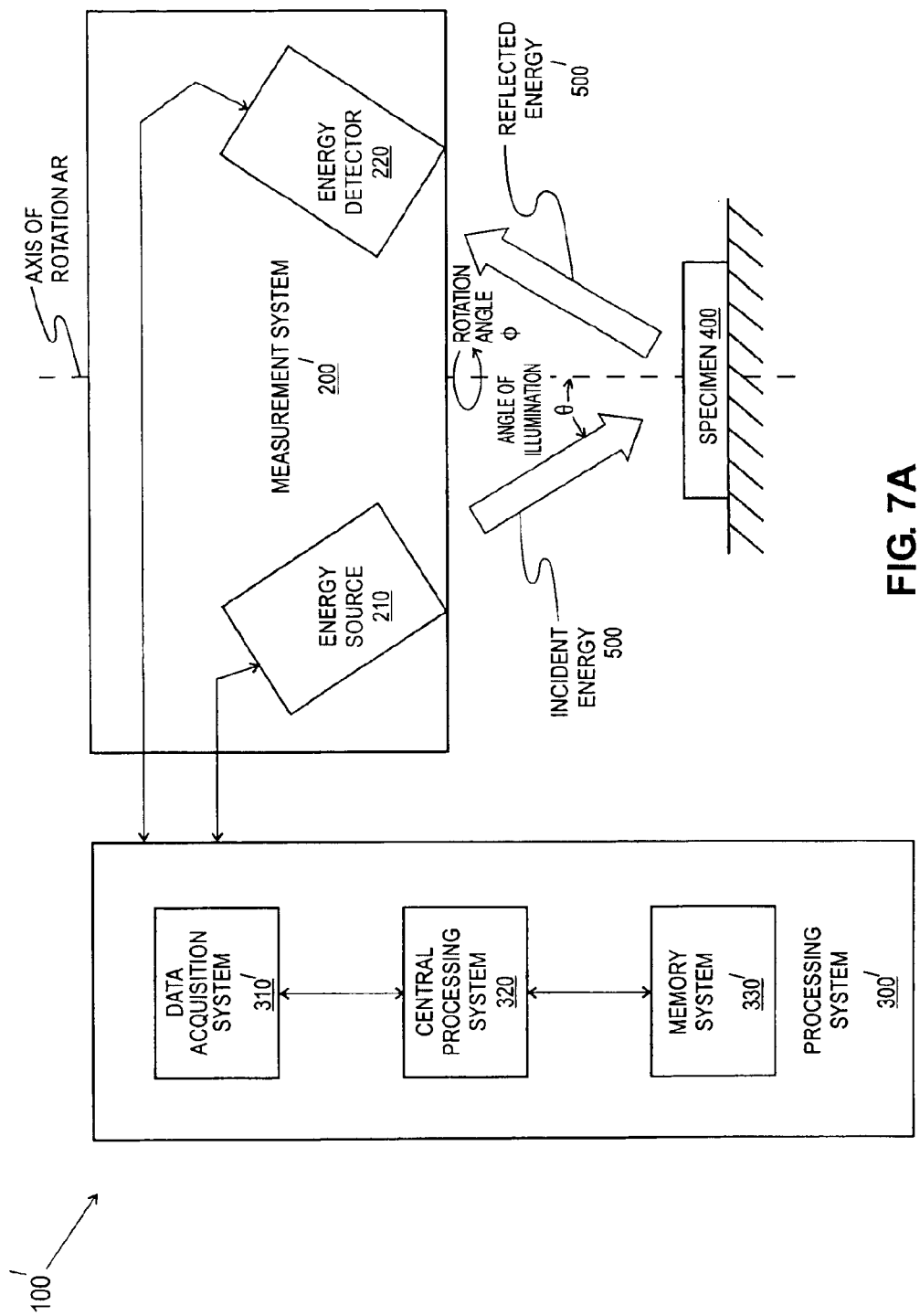
FIG. 7A is a detail drawing illustrating one embodiment of a processing system for the metrology system of FIG. 3.

One embodiment of a processing system 300' for metrology systems 100' is illustrated in FIG. 7A. The processing system 300' is configured to receive the data signals from the measurement system 200' and to analyze the data signals to determine whether the structure 410 (shown in FIG. 2) formed on the specimen 400 has any defects. As shown in FIG. 7A, the processing system 300' comprises a data acquisition system 310', a central processing system 320', and a memory system 330'. The data acquisition system 310' is configured to receive the data signals and, as desired, to convert the data signals into digital data (not shown). In a preferred embodiment, the data acquisition system 310' includes at least one analog-to-digital conversion (ADC) system for digitizing the data signals.

Being configured to perform the analysis of the digital data, the central processing system 320' can comprise any type of processing system, such as one or more central processing units (CPUs) and/or digital signal processors (DSPs), and is configured to communicate with the data acquisition system 310' and the memory system 330'. The central processing system 320' thereby can receive the digital data from acquisition system 310' and/or the memory system 330'. In other words, the central processing system 320' can perform the analysis of the digital data in real-time and/or can store the digital data in the memory system 330' for later retrieval and analysis. The digital data preferably is stored in the memory system 330' such that the association between the digital data and the rotation angle $\phi$ is substantially maintained. If each rotation angle $\phi$ is associated with a memory register (not shown), for example, the digital data for each rotation angle $\phi$ can be stored in the relevant memory register. Similarly, the digital data and the associated rotation angle $\phi$ can be stored in the memory system 330' in the form of a look-up table.

Comprising any suitable type of memory system, the memory system 330' can include volatile memory and/or non-volatile memory of any kind and can be configured to store and provide other types of information. For example, the central processing system 320' can perform the data analysis by receiving and executing a series of instructions, which can be provided in the form of instruction code, such as software or firmware, that is stored in the memory system 330'. The partial and/or complete results of the analysis likewise can be stored in, and retrievable from, the memory system 330'. As desired, the central processing system 320' can analyze the digital data as the data signals are successively received by the processing system 300', and/or the analysis can be delayed until substantially the complete spectrum of data signals has been received.

The central processing system 320' can perform the analysis of the digital data in any suitable manner. For example, the analysis of the digital data can be performed via a neural network (not shown). The neural network can be trained to identify preferred spectra of digital data by examining a plurality of sample specimens 400. By analyzing a wide range of good and bad sample specimens 400, the neural network can "learn" to identify spectra associated with preselected structural defects.

Figure 7B:
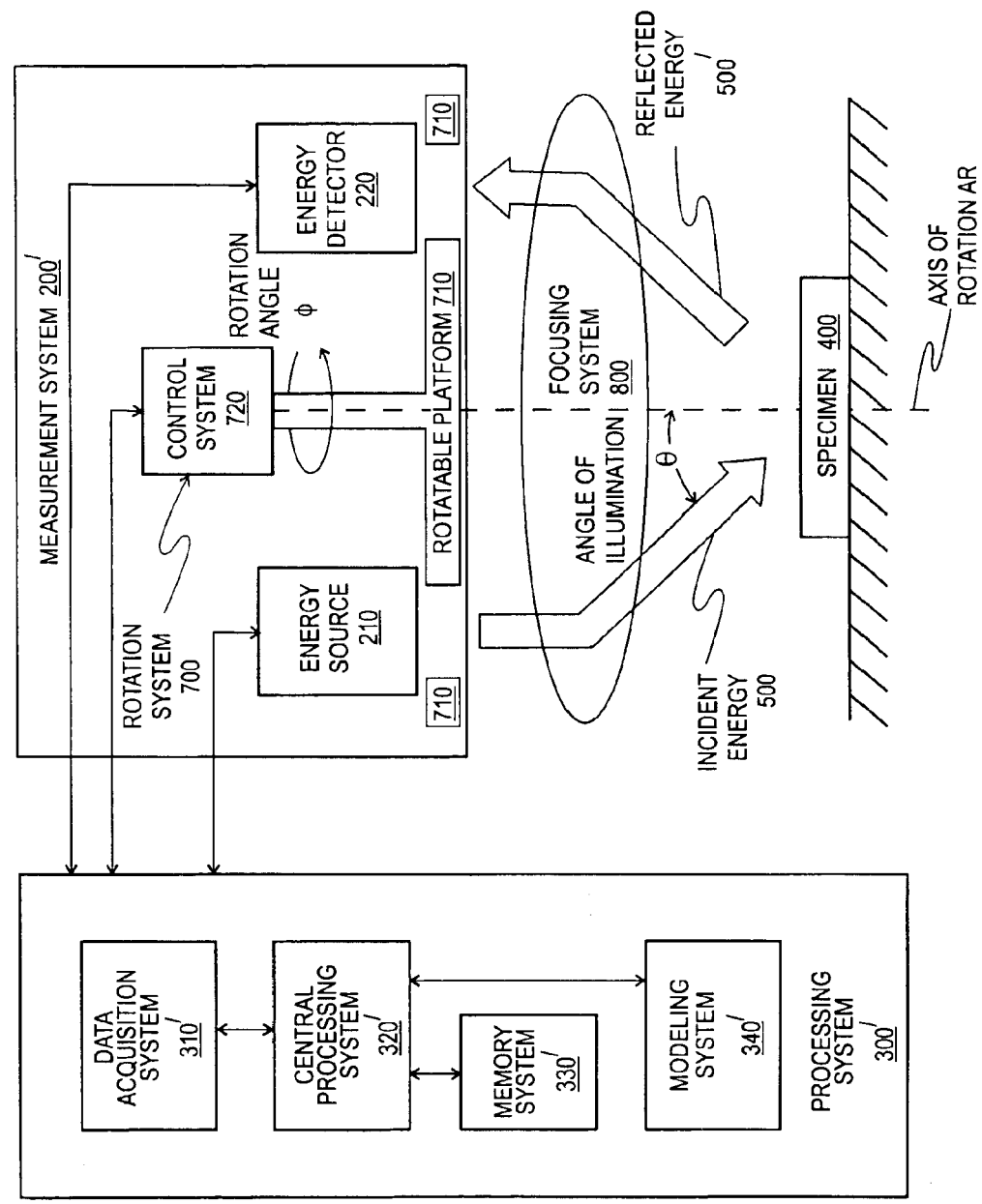
FIG. 7B is a detail drawing illustrating an alternative embodiment of the processing system of FIG. 7A.

In another embodiment, the central processing system 320' is configured to perform the data analysis by comparing the digital data with one or more mathematical models (not shown) of the structure 410 as illustrated by the processing system 300" of the metrology system 100" shown in FIG. 7B. Being provided substantially in the manner discussed above with reference to the processing system 300' (shown in FIG. 7A), the processing system 300" comprises a data acquisition system 310", a central processing system 320", and a memory system 330" and further includes a modeling system 340". As desired, the modeling system 340" can be combined with, or substantially separate from, the memory system 330".

The modeling system 340" is configured to provide at least one mathematical model of the structure 410. Each mathematical model typically is calculated based upon input parameters regarding ideal dimensions of the structure 410 as well as other information, such as user-provided information. Upon receiving the digital data, the central processing system 320" is configured to compare the digital data with the mathematical model in any suitable manner, such as by performing a minimization procedure, such as a minimization procedure involving nonlinear regression. Similarly, model data (not shown) can be precalculated for each mathematical model and stored in the modeling system 340", preferably in the form of a look-up table. The central processing system 320" thereby can perform the data analysis by comparing the digital data with the model data. The processing system 300 (shown in FIG. 2) is shown and described herein as comprising the processing system 300' in FIG. 7A and the processing system 300" in FIG. 7B for purposes of illustration only. The processing system 300 can be any suitable type of processing system and is not limited to the illustrated embodiments. Likewise, it is understood that the measurement system 200 (shown in FIG. 2) can comprise any suitable type of measurement system and is not limited to the exemplary measurement systems 200', 200" shown and described with reference to FIGS. 3 and 6A and FIG. 7B, respectively.

It also will be appreciated that the incident energy 500 and/or the reflected energy 500' can propagate between the measurement system 200' substantially directly as illustrated in FIG. 7A or via one or more intermediate systems, such as the focusing system 800 shown in FIG. 7B. Being disposed substantially between the measurement system 200' and the specimen 400, the focusing system 800 is configured to focus the incident energy 500, the reflected energy 500' and/or the scattered energy 520 (shown in FIGS. 2 and 8). Illustrative focusing system 800 are disclosed in U.S. Pat. No. 5,604,334, issued to Finarov, and U.S. Pat. No. 6,124, 924, issued to Feldman et al., each of which are hereby expressly incorporated herein by reference.

If the energy source 210 is a monochromatic light source, such as a laser, for example, the focusing system 800 can be a lens or a lens system, such as a microscope objective; whereas, the focusing system 800 can comprise radiation-reflective focusing optics when the energy source 210 is a broadband source. Likewise, the focusing system 800 can include a bent crystal if the energy source 210 emits incident energy 500 with a preselected wavelength $\lambda$ that is substantially in the x-ray band. As desired, the focusing system 800 can include the beam-formation system 215 discussed in more detail above with regard to FIGS. 4A–B and/or the energy-collection system 225 discussed in more detail above with reference to FIGS. 5A–B.

Returning to FIG. 3, the metrology system 100 can further include a platform 600 for supporting the specimen 400. The platform 600 can comprise any suitable type of platform, such as a vacuum chuck or an electrostatic chuck, such that the specimen 400 is secured substantially in place. In the manner described above, depending, at least in part, upon the nature of the specific application for which the metrology system 100 is to be utilized, the platform 600 can be a motorized translation platform, or any other suitable mechanical device or system known in the art. Specifically, a motorized translation stage can be employed such that different portions, such as multiple structures 410, of the specimen 400 can be characterized by the metrology system 100. Although illustrated in FIG. 3 as being uncoupled from the measurement system 200' and the processing system

300, it is understood that the platform 600 can be coupled with, and configured to communicate with, the measurement system 200' and/or the processing system 300 as desired.

The relative rotation between the measurement system 200' and the specimen 400 can be achieved in any manner such as by rotating the measurement system 200'. For example, FIG. 7B illustrates a rotation system 700 that is configured to rotate the measurement system 200' substantially about the axis of rotation AR to achieve the relative rotation between the measurement system 200' and the specimen 400. As shown in FIG. 7B, the rotation system 700 comprises a rotatable platform 710 and a control system 720. The rotatable platform 710 is fixedly coupled with the energy source 210 and the energy detector 220 of the measurement system 200'. The control system 720 can comprise any suitable type of control system, such as a motor, and, as shown in FIG. 7B, can be coupled with the processing system 300". Thereby, the operation of the control system 720, and therefore the rotation of the measurement system 200', is controllable via the processing system 300".

The control system 720 can further include an encoding system (not shown) that is configured to produce a rotational data signal (not shown) that represents the rotation angle $\phi$ of the rotatable platform 710 and to provide the rotational data signal to the processing system 300". The rotational data signal can provide feedback to the processing system 300" when the processing system 300" is configured to control the rotation of the measurement system 200'. Further, the processing system 300" can utilize the rotational data signal to associate the relevant rotation angle $\phi$ with the relevant data signal and/or the digital data produced therefrom, for example, when storing the digital data in the memory system 330" in the manner discussed in more detail above with reference to the processing system 300".

Although shown and described as comprising the rotation system 700 in FIG. 7B for purposes of illustration, it is understood that the relative rotation between the measurement system 200 and the specimen 400 can be achieved by way of any suitable rotation system and is not limited to the illustrated embodiment. For example, the relative rotation can be carried out electronically, such as by employing a measurement system 200 as shown in FIG. 8 that comprises an array 210' of energy sources 210A–F and an array 220' of energy detectors 220A–F. The array 210' can comprise any number of energy sources 210A–F, each being provided in the manner set forth in more detail above with reference to FIGS. 3 and 4A–B; Likewise, the array 220' can include any number of energy detectors 220. Each of the energy detectors 220A–F in the array 220' are provided in the manner set forth in more detail above with reference to FIGS. 3 and 5A–B. Each of the arrays 210', 220' can be disposed, partially or substantially completely, around the specimen 400 in substantially any suitable arrangement or configuration, and each energy source 210 in the array 210' is associated with at least one energy detector 220 in the array 220'.

As shown in FIG. 8, the arrays 210', 220' are provided in the bright field detection configuration (shown in FIG. 6B) and are partially disposed around the specimen 400. Energy source 210A is configured to direct incident energy 500A toward the specimen 400 and is associated with energy detector 220A. The energy detector 220A is configured to receive a portion of the incident energy 500A that reflects from the specimen 400 as reflected energy 500A'. Being associated with energy detector 220B, energy source 210B can direct incident energy 500B toward the specimen 400 at a predetermined angle $\phi_{AB}$ relative to the incident energy 500A provided by the energy detector 220A. A portion of the incident energy 500B that reflects from the specimen 400 is received by the energy detector 220B as reflected energy 500B'. Similarly, energy sources 210C–F respectively direct incident energies 500C–F toward the specimen 400 at predetermined angles $\phi_{BC}$, $\phi_{CD}$, $\phi_{DE}$, and $\phi_{EF}$ relative to the incident energies 500B–E, respectively. The incident energies 500C–F reflect from the specimen 400 as reflected energies 500C–F', a portion of which is received by energy detectors 220C–F, respectively.

The predetermined angles $\phi_{AB}$, $\phi_{BC}$, $\phi_{CD}$, $\phi_{DE}$, and $\phi_{EF}$ can comprise any suitable angle and preferably are substantially equal. Similarly, the energy detectors 220A–F preferably are configured to provide the incident energies 500A–F with substantially the same characteristics. Thereby, when the energy detectors 220A–F are successively activated, the incident energies 500A–F are successively directed toward the specimen 400, and the energy detectors 220A–F successively receive the reflected energies 500A–F' such that the measurement system 200 is virtually rotated relative to the specimen 400.

Upon receiving the reflected energies 500A–F', the measurement system 200 can produce the spectrum of data signals therefrom and provide the spectrum of data signals to the processing system 300 (shown in FIG. 3) in the manner discussed in more detail above. Likewise, the processing system 300 can perform an analysis of the spectrum of data signals in the manner set forth above to determine whether the structure 410 has any defects. Electronic rotation can reduce the time required to produce the spectrum of data signals, which time reduction is highly desirable for in line metrology and process monitoring of semiconductor wafers during processing.

It will be appreciated that electronic rotation likewise can be performed with the arrays 210', 220' in the dark field detection configuration discussed above with reference to FIG. 6A. Furthermore, by associating more than one energy detector 220 with an energy source 210, the measurement system 200 is configured to be in both the bright field and the dark field detection configurations. If the energy detectors 220A, 220C are associated with the energy source 210A, for example, the measurement system 200 is configured to receive and analyze the reflected energy 500A' via the energy detector 220A and the scattered energy 520 (shown in FIG. 2) via the energy detector 220C. Thereby, the metrology system 100 substantially simultaneously receive and analyze bright field and dark field data signals.

The details of the operation of the metrology system 100" will be presently discussed with reference to FIGS. 6B, 7B, 8, and 9. Although a bright field detection configuration of the energy source 210 and the energy detector 220 as shown in FIG. 6B is assumed for purposes of illustration, it is understood that the present discussion can equally apply to a dark field detection configuration of FIG. 6A. FIG. 9 is a three-dimensional view of an exemplary structure 410 formed on the specimen 400. For purposes of simplicity, the exemplary structure 410 is illustrated in FIG. 9 as a plurality of substantially parallel trenches 430 formed in the specimen 400 and defined by internal surfaces 440. It is understood, however, that any surface in which the reflectivity or impedance is a function of angle can be characterized by the metrology system 100". In the manner discussed in more detail above with reference to FIG. 7B, the metrology system 100" is configured to rotate the measurement system 200 along the axis of rotation AR, which preferably is substantially perpendicular to the external surface 420 of the specimen 400 and intersects the structure 410.

In operation, the energy source 210 provides the beam of incident energy 500, which propagates toward the specimen 400 substantially at the angle of illumination θ relative to the axis of rotation AR. Upon reaching the specimen 400, the incident energy 500 reflects from the specimen 400. As shown in FIG. 9, some of the incident energy 500 rebounds from the specimen 400 in various directions as scattered energy 520; whereas, a portion of the incident energy 500 reflects toward the energy detector 220 as reflected energy 500' in the manner discussed in more detail above with reference to FIG. 2. The energy detector 220 receives and detects the reflected energy 500' and produces data signals therefrom. Although the data signals can be any suitable type of information regarding the reflected energy 500', such as an amplitude, a frequency, a phase change, and/or a power level, the data signals are shown and described as comprising a power level of the reflected energy 500' for purposes of this example.

As the metrology system 100" rotates the energy source 210 and the energy detector 220 about the axis of rotation AR, the incident energy 500 propagates toward, and therefore reflects from, the external and internal surfaces 420, 440 from different rotation angles φ. The power level of the reflected energy 500' as received by the energy detector 220 therefore can vary as a function of the rotation angle φ. For instance, when the energy source 210 and the energy detector 220 are substantially perpendicular to the trenches 430, a relatively large portion of the incident energy 500 is reflected by the internal surfaces 440 as scattered energy 520, and the power level of the reflected energy 500' as measured by the energy detector 220 is relatively low. In contrast, a lesser portion of the incident energy 500 is reflected by the internal surfaces 440 as scattered energy 520 when the energy source 210 and the energy detector 220 are substantially in parallel with the trenches 430. The energy detector 220 therefore measures reflected energy 500' with a higher power level.

In the manner described in more detail above with reference to FIG. 3, the measurement system 200' produces a spectrum of measured power data signals from the measured power levels. The measurement system 200' provides the spectrum of measured power data signals as well as the rotational data signals produced by the rotation system 700 to the processing system 300". Upon receiving the spectrum of measured power data signals and the rotational data signals, the processing system 300" produces digital measured power data therefrom, which digital measured power data is associated with the relevant rotation angles φ, in the manner discussed in more detail above with reference to FIG. 7A. Thereby, the measured power spectrum PS comprises the measured power level as a function of rotation angles φ and is illustrated in FIG. 10 is produced.

The modeling system 340" of the processing system 300" preferably includes at least one mathematical model of the structure 410 of FIG. 9. Since the measurement system 200' is configured to measure the power level of the reflected energy 500' in this example, the relevant mathematical model likewise comprises the measured power level as a function of rotation angles φ and is illustrated as a model power spectrum MS in FIG. 10. The processing system 300" performs an analysis of the exemplary structure 410 of FIG. 9 by comparing the measured power spectrum PS with the model power spectrum MS. Thereby, the metrology system 100" can determine whether the structure 410 has any defects.

It will be appreciated that the operation of the metrology system 100" can be modified in accordance with the nature of the specific application for which the metrology system 100" is to be utilized. Illustrative factors for identifying suitable configurations include the dimensions and complexity of the structure 410 being characterized, the materials from which the structure 410 is formed, and the desired precision of the characterization results. By the adjusting the operation of the metrology system 100", the metrology system 100" can be configured to analyze more complex structures 410, to increase the precision of the characterization results, to more quickly characterize the structure 410, and to yield additional information with regard to the structure 410.

For example, the metrology system 100" can be configured to analyze a different number of data signals when characterizing the structure 410. The number of data signals can be adjusted by modifying the range of the rotation angle φ by which the metrology system 100" rotates the measurement system 200" relative to the specimen 400 and/or by changing the number of measurement that measurement system 200" makes per revolution relative to the specimen 400. The range of rotation angles φ can comprise any suitable range of angles, including ranges that exceed a complete revolution of the revolution of the measurement system 200" relative to the specimen 400. Stated somewhat differently, the range of rotation angles φ can be greater than, less than, or substantially equal to a complete revolution of three hundred and sixty degrees (360°). By increasing the number of data signals, the metrology system 100" can be configured to analyze more complex structures 410 and/or increase the precision of the characterization results.

The operation of the metrology system 100" likewise can be modified by permitting other operational parameters of the metrology system 100", such as the angle of illumination θ, the polarization of the incident energy 500, and/or the wavelength λ (shown in FIG. 3) of the incident energy 500, to be adjustable. Although each was presumed to be substantially constant in the above example, the angle of illumination θ and/or the wavelength λ of the incident energy 500 can be adjustable. In the manner discussed in more detail above with reference to FIG. 3, the angle of illumination θ can be adjustable within a predetermined range of angles. Likewise, when the incident energy 500 comprises electromagnetic radiation, for example, the wavelength λ of the incident energy 500 can vary among a plurality of predetermined wavelengths, such as a sweep of successive wavelengths, each being substantially within a predetermined range in the manner discussed above with regard to FIG. 3.

The angle of illumination θ and/or the wavelength λ of the incident energy 500 can be adjustable via the processing system 300" and/or independently of the processing system 300". In addition to receiving the data signals and the rotational data signal, the processing system 300" also can receive one or more control signals (not shown) that represent the angle of illumination θ and/or the wavelength λ of the incident energy 500. These control signals can be provided, and associated with the data signals, substantially in the manner discussed above with regard to the rotational data signals. Furthermore, the control signals can provide feedback to the processing system 300" when the processing system 300" is configured to control the angle of illumination θ and/or the wavelength λ of the incident energy 500.

The angle of illumination θ and/or the wavelength λ of the incident energy 500 can be adjustable relative to the rotation angle φ. Stated somewhat differently, the metrology system 100" can be configured to adjust the rotation angle φ, the angle of illumination θ, and/or the wavelength λ either in isolation or substantially simultaneously in any combination. For example, the angle of illumination θ and/or the wavelength λ of the incident energy 500 can be held substantially fixed for a substantially complete revolution of the measurement system 200" relative to the specimen 400. The angle of illumination θ and/or the wavelength λ of the incident energy 500 likewise can be varied as the measurement system 200" rotates relative to the specimen 400. FIGS. 11A–B provide exemplary three-dimensional measured power spectrum characterizations PS', PS" of the structure 410 shown in FIG. 9. By permitting other operational parameters of the metrology system 100" to be adjustable, the metrology system 100" can be configured to analyze more complex structures 410 and/or increase the precision of the characterization results.

Figure 12:
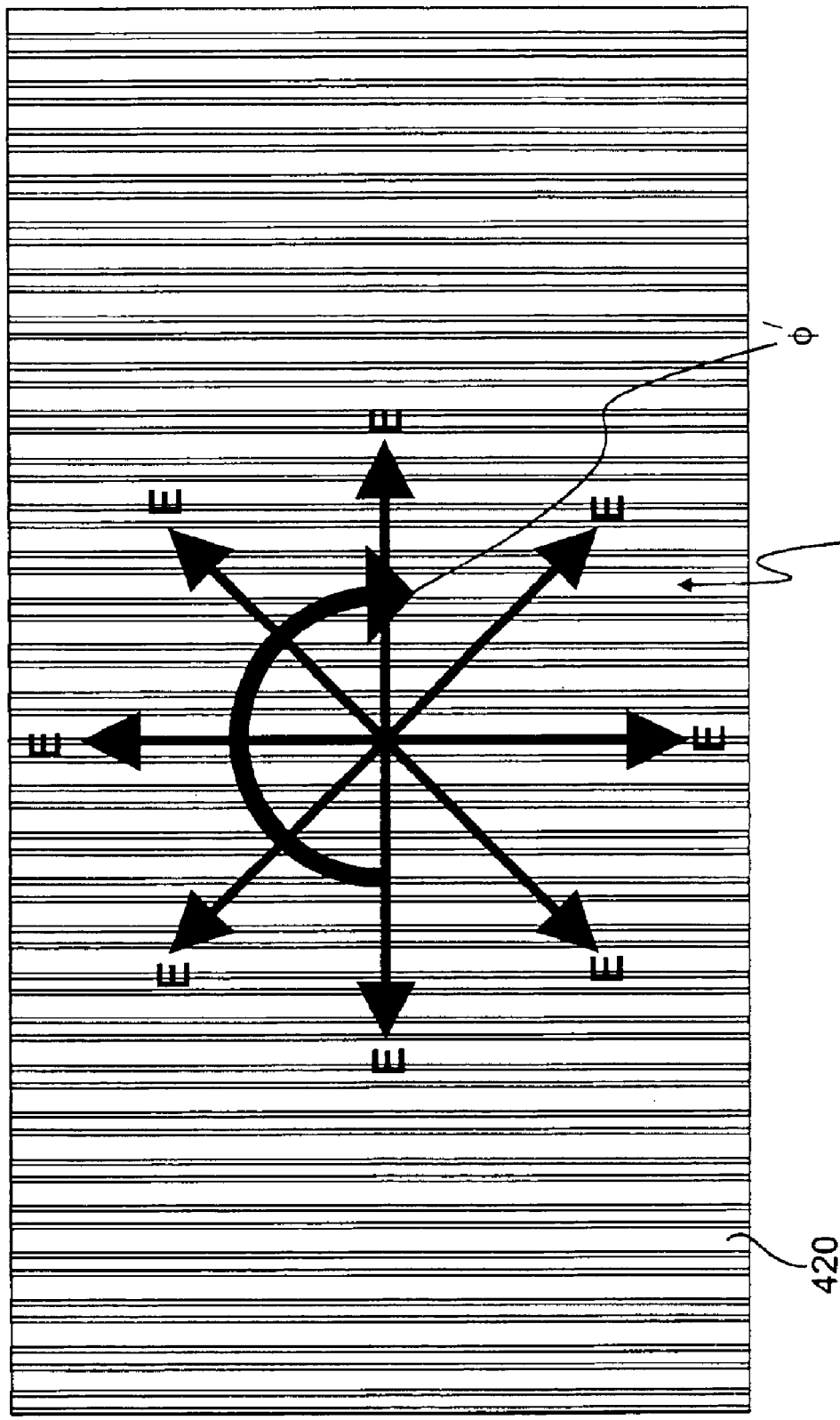
FIG. 12 illustrates an electric field of incident energy provided by the energy source of FIGS. 4A–B.

FIG. 11 illustrates an electric field E of the incident energy 500 incident on the surface 420 and is discussed with reference to the metrology system 100 shown in FIG. 3. As shown in FIG. 12, the surface 420 includes a grating 450. The incident energy 500 comprises a propagating wave with a S-type polarization such that the electric field E is substantially perpendicular to the plane of incidence PI (shown in FIG. 9) defined by the incident energy 500 and the reflected energy 500'. As the energy source 210 rotates though the rotation angle φ relative to the specimen 400, the electric field E on the surface 420 of the specimen 400 forms an angle φ' relative to the grating 450, which angle φ' is approximately equal to the rotation angle φ. It will be appreciated that, for each angle φ', the surface 420 can have a different impedances at microwave frequencies and a different reflectivities at optical and/or X-ray wavelengths λ.

For surfaces 420 that are substantially smooth and isotropic, the field boundary conditions are approximately the same for each rotation angle φ at which these surfaces 420 are being interrogated. The field boundary conditions however can differ for each rotation angle φ if the surface 420, such as the grating 450 shown in FIG. 12, is not substantially smooth and isotropic. These differences in the field boundary conditions can result in a different reflectivity for the surface 420 for each rotation angle φ. Since these differences exist in the phase and/or the amplitude of the complex reflection coefficient, the term "reflectivity" can refer to the usage of the phase and/or the intensity. As such, intensity and/or phase spectra can be obtained with respect to the angle φ', and, furthermore, such spectra can be obtained with different input polarizations.

It will be appreciated that the grating 450 can be viewed as a plurality of closely-spaced, coupled electromagnetic waveguides. When the incident energy 500 reaches the surface 420, a wave (not shown) is launched in these waveguides, and any associated coupling and resonances can be a function of the characteristics of the incident energy 500. The characteristics of the incident energy 500 include the angle of illumination θ, rotation angle φ, and the polarization of the incident energy 500. Further, in spectroscopic reflectometry and ellipsometry, a change in the angle of illumination θ and/or the wavelength λ (shown in FIG. 3) of the incident energy 500 can produce a change in the spectrum even if the surface 420 is substantially smooth and isotropic. Here, on the other hand, a change in the spectrum with respect to the rotation angle φ will result only if the surface 420 includes the grating 450 or any other three-dimensional structure, such as structure 410 (shown in FIG. 2). The three-dimensional properties of the grating 450 therefore are being analyzed rather than the two-dimensional properties of the surface 420.

Figure 13A:
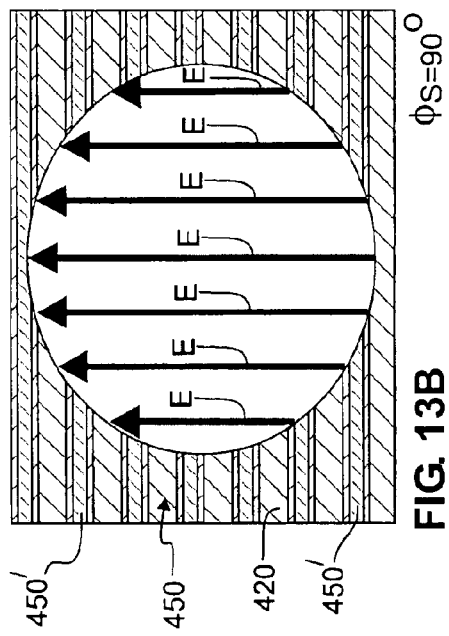
FIG. 13A illustrates the incident energy of FIG. 12 having a S-polarization and propagating substantially perpendicularly toward the grating lines of a grating structure.
Figure 13B:
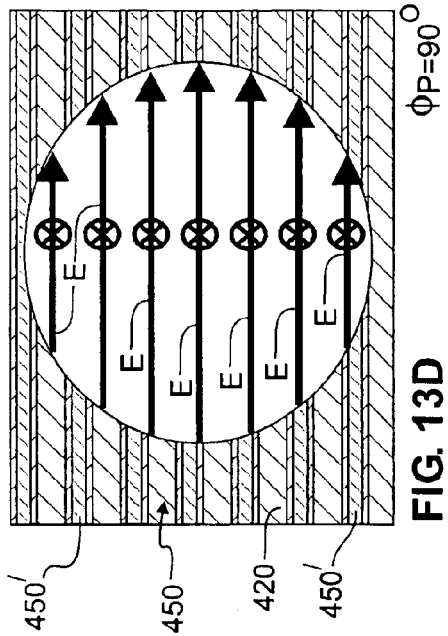
FIG. 13B illustrates the incident energy of FIG. 13A propagating toward grating structure substantially in parallel with the grating lines.

FIGS. 13A–D illustrate the polarization of the electric field E of the incident energy 500 and is discussed with reference to the metrology system 100 shown in FIG. 3. As illustrated in FIGS. 13A–D, the surface 420 includes the grating 450, which comprises a plurality of substantially parallel grating lines 450'. Turning to FIG. 13A, the incident energy 500 is shown as having the electric field E with S-polarization and as propagating toward the grating 450 at an rotation angle φ that is substantially equal to zero degrees (0°). In other words, the incident energy 500 is substantially perpendicular to the grating lines 450'. The electric field E of the incident energy 500 therefore is substantially parallel to the grating lines 450'. The incident energy 500 illustrated in FIG. 13B likewise has the electric field E with the S-polarization but propagates toward the grating 450 at an rotation angle φ that is substantially equal to ninety degrees (90°). Since the incident energy 500 is substantially in parallel with the grating lines 450', the electric field E is substantially perpendicular to the grating lines 450' as shown in FIG. 13B.

Figure 13C:
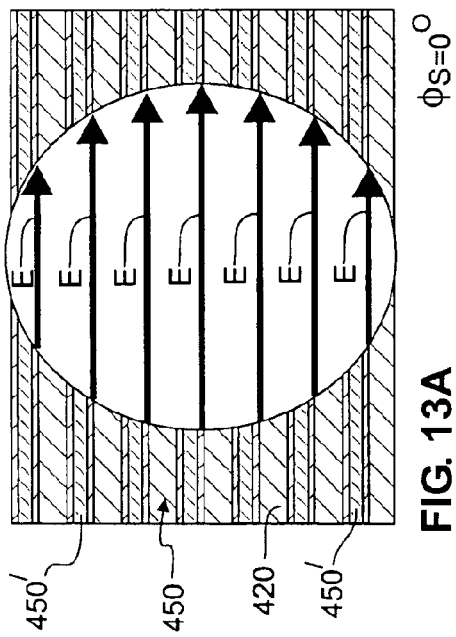
FIG. 13C illustrates the incident energy of FIG. 12 having a P-polarization and propagating substantially perpendicularly toward the grating lines of a grating structure.
Figure 13D:
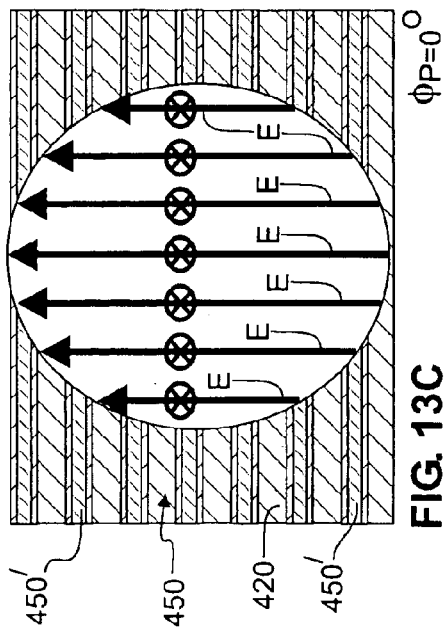
FIG. 13D illustrates the incident energy of FIG. 13C propagating toward grating structure substantially in parallel with the grating lines.

Similarly, FIGS. 13C–D illustrate the incident energy 500 with the electric field E having P-polarization. In the P-polarization, the electric field E is substantially in the plane of incidence PI (shown in FIG. 9) and has a tangential component and a perpendicular component. The tangential component is substantially parallel to the surface 420; whereas, the perpendicular component is substantially perpendicular to the surface 420. In FIG. 13C, the incident energy 500 is shown as propagating toward the grating 450 at an rotation angle φ that is substantially equal to zero degrees (0°). Since the incident energy 500 is substantially perpendicular to the grating lines 450', the electric field likewise is substantially perpendicular to the grating lines 450' and has a field component E' that is substantially normal to the surface 450. The incident energy 500 that propagates toward the grating 450 at an rotation angle φ that is substantially equal to ninety degrees (90°) is illustrated in FIG. 13D. Here, the incident energy 500 is substantially parallel to the grating lines 450' such that the electric field E also is substantially parallel to the grating lines 450'. In the manner discussed above with reference to FIG. 13C, the field component E' of the electric field E is substantially normal to the surface 450.

Figure 14A:
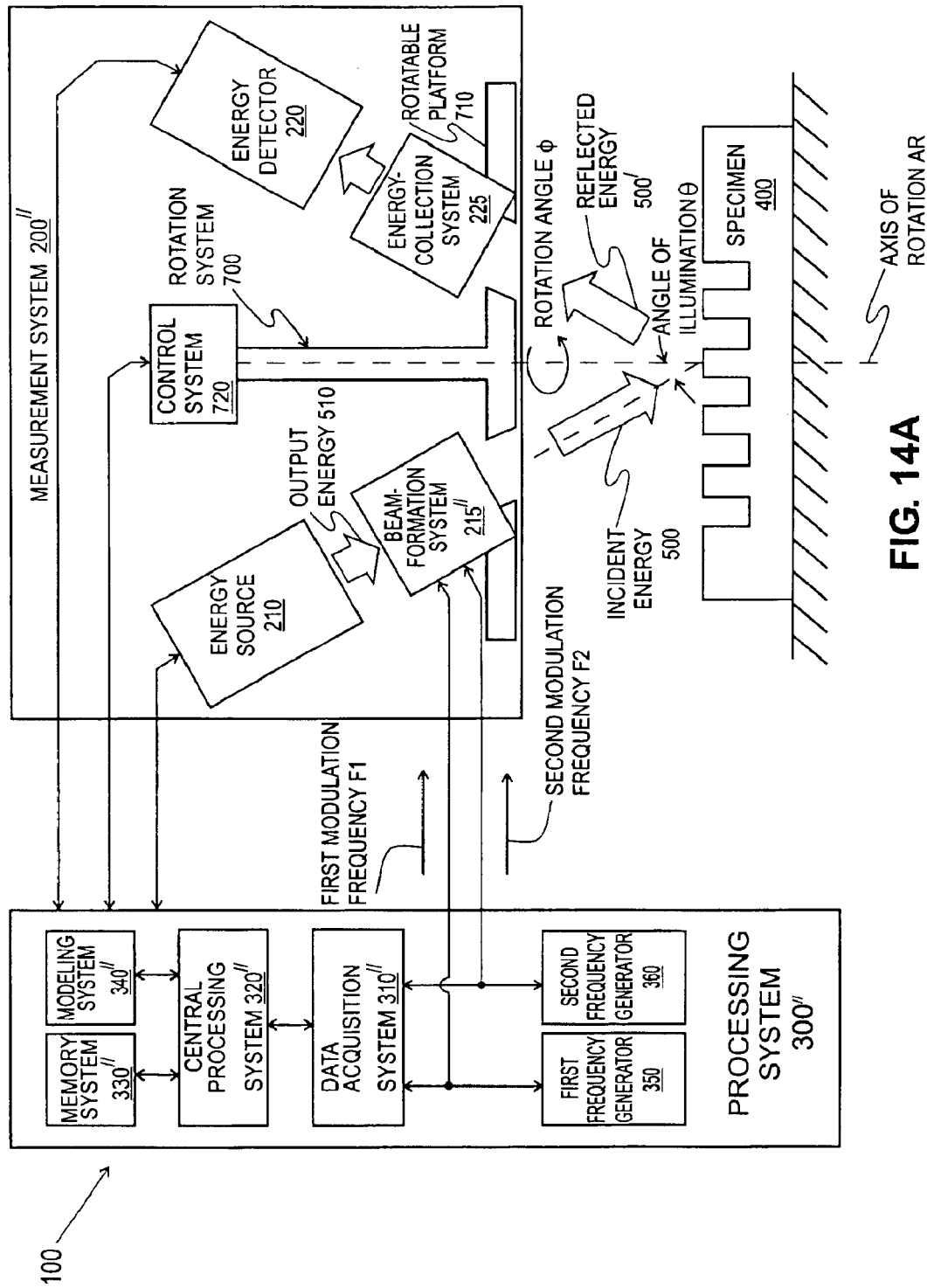
FIG. 14A is an exemplary block diagram illustrating an alternative embodiment of the metrology system of FIG. 2.
Figure 14B:
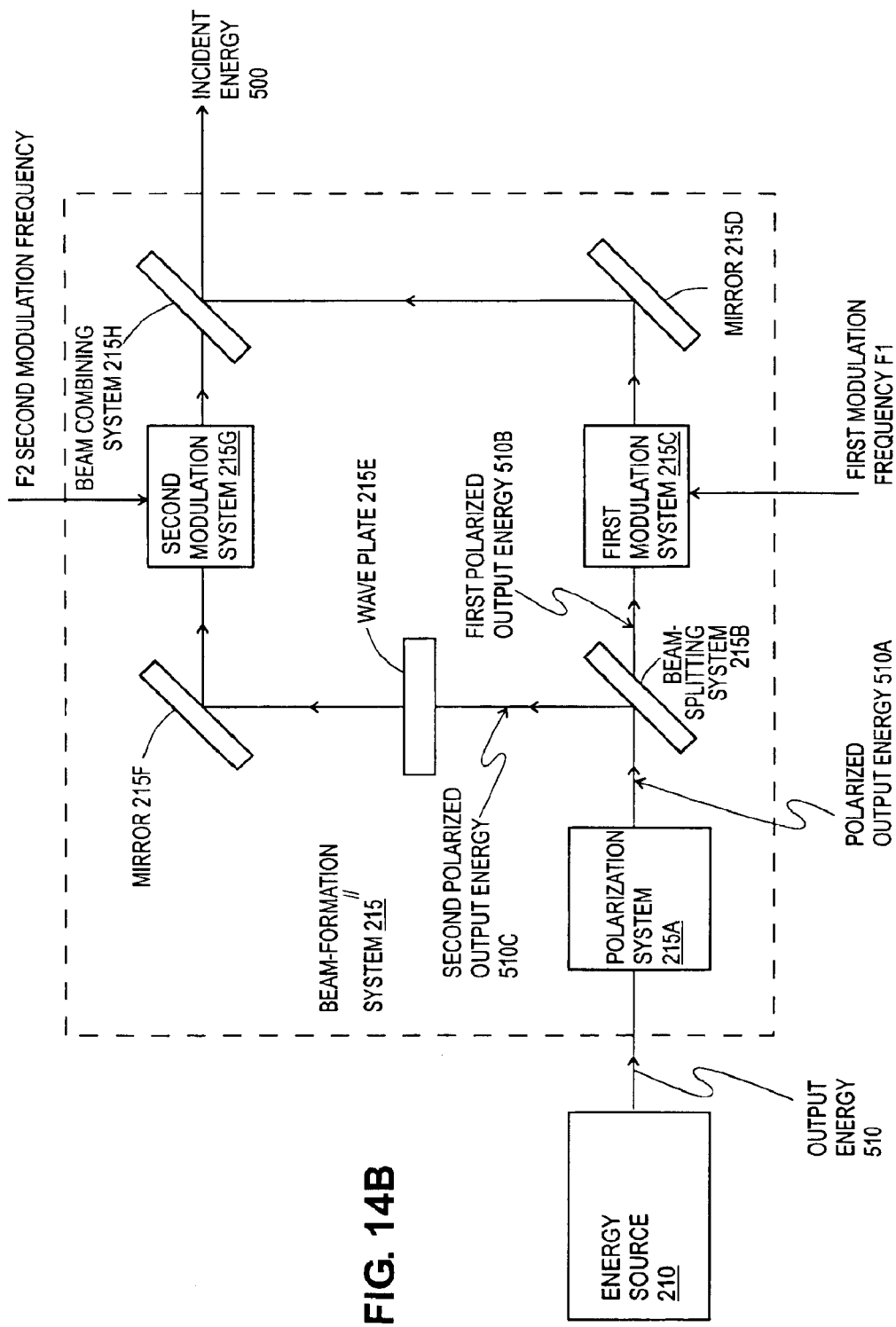
FIG. 14B is a detail drawing illustrating one embodiment of a beam-formation system for the metrology system of FIG. 14A.

Another embodiment of the metrology system 100 (shown in FIG. 2) is illustrated as the metrology system 100" in FIGS. 14A–B. In the manner discussed in more detail above with reference to the metrology system 100' (shown in FIG. 7), the metrology system 100" includes a measurement system 200" that is coupled with, and configured to communicate with, a processing system 300" as shown in FIG. 14A. Being configured to characterize a three-dimensional structure 410 (shown in FIG. 2) formed on a specimen 400, the metrology system 100" can rotate the measurement system 200" relative to the specimen 400 while the measurement system 200" directs a beam of incident energy 500 toward the specimen 400. As illustrated in FIG. 14A, the rotation of the measurement system 200" relative to specimen 400 is performed along an axis of rotation AR that preferably is substantially perpendicular to an external surface 420 of the specimen 400 and intersects the structure 410. Propagating toward the specimen 400 substantially at an angle of illumination θ relative to the axis of rotation AR, the incident energy 500 reflects from the surface 420 as reflected energy 500', at least a portion of which propagates toward the measurement system 200".

The measurement system 200" also is configured to receive the reflected energy 500' and to produce data signals (not shown) therefrom, providing the data signals to the processing system 300". As the relative rotation continues, the measurement system 200" receives reflected energy 500' associated with each of a plurality of rotation angles φ and produces additional data signals, which likewise are provided to the processing system 300". Thereby, a spectrum of data signals is produced with respect to the rotation angle φ. Receiving the spectrum of data signals, in whole or in part, from the measurement system 200", the processing system 300" is configured to perform an analysis of the data signals to determine whether the structure 410 has any defects, such as yield limiting deviations or other processing defects. The processing system 300" can analyze the data signals in any suitable manner, such as by comparing the data signals with one or more mathematical models (not shown) of the structure 410.

As shown in FIG. 14A, the measurement system 200" comprises an energy source 210, an energy detector 220, and a rotation system 700, each being provided in the manner discussed in more detail above with reference to FIGS. 3, 4A–B, 5A–B, and 7. Typically being coupled and preferably being substantially fixedly coupled, the energy source 210 and the energy detector 220 are approximately uniformly disposed about, and substantially in axial alignment with, the axis of rotation AR. Thereby, the rotation system 700 is configured to rotate the energy source 210 and the energy detector 220 around the axis of rotation AR relative to the specimen 400.

The measurement system 200" further includes a beam-formation system 215" and an energy-collection system 225. In the manner described above with reference to FIGS. 4A–B, the beam-formation system 215" is disposed substantially between the energy source 210 and the specimen 400 and is configured to receive output energy 510 from the energy source 210 and to convert the output energy 510 into the beam of incident energy 500. The energy-collection system 225 is provided in the manner described above with reference to FIGS. 5A–B and is disposed substantially between the specimen 400 and the energy detector 220. The energy-collection system 225 is configured to receive the reflections of the incident energy 500 from the specimen 400 and to convert these reflections into the reflected energy 500' in the manner described above with reference to FIGS. 5A–B. Being shown in FIG. 14A as being separate from the energy source 210 and the energy detector 220, respectively, for purposes of illustration, it will be appreciated that the beam-formation system 215" can be disposed substantially within the energy source 210 as illustrated in FIG. 4A, and/or the energy-collection system 225 can be disposed substantially within the energy detector 220 as illustrated in FIG. 5A.

Upon receiving the output energy 510 from the energy source 210, the beam-formation system 215" is configured to divide the output energy 510 into a plurality of components and to modulate each component at a preselected frequency. The modulated components then are recombined to form the beam of incident energy 500. One embodiment of the beam-formation system 215" is illustrated in FIG. 14B. As shown in FIG. 14B, the beam-formation system 215" is configured to divide the output energy 510 into two components. If the output energy 510 comprises electromagnetic energy, for example, the components can be a S-polarized component and a P-polarized component of the output energy 510.

The beam-formation system 215" includes a polarization system 215A that is configured to receive the output energy 510 to provide polarized output energy 510A. A beam-splitting system 215B is coupled with the polarization system 215A and can receive the polarized output energy 510A, dividing the polarized output energy 510A into first and second polarized output energy 510B, 510C. The first polarized output energy 510B is provided to a first modulation system 215C, which is configured to modulate the first polarized output energy 510B at a first preselected modulation frequency F1, and then is provided to a beam-combining system 215H via a mirror 215D.

The polarized output energy 510C is provided to a wave plate 215E. Preferably comprising a one-half wave plate, the wave plate 215E is configured to modify the polarization of the polarized output energy 510C, such as by approximately ninety degrees (90°). The polarized output energy 510C, as modified, is provided to a second modulation system 215G via a mirror 215F. The second modulation system 215G is configured to modulate the second polarized output energy 510C at a second preselected modulation frequency F2 and to provide the second polarized output energy 510C, as modified and modulated, to the beam-combining system 215H. The beam-combining system 215H combines the modulated first polarized output energy 510B with the second polarized output energy 510C, as modified and modulated, to form the resultant beam of incident energy 500.

Returning to FIG. 14A, the resultant beam of incident energy 500 is directed toward the specimen 400 in the manner described in more detail above. The reflected energy 500' is received by the energy-collection system 225, which analyzes the polarization of the reflected energy 500' before providing the reflected energy 500' to the energy detector 220. Since the beam of incident energy 500 includes two polarization states, each being modulated at a different preselected frequency, the reflected energy 500' received by the energy detector 220 substantially comprises two sets of information. In other words, each polarization state may be processed by the measurement system 200 as two separate operands.

Many operations therefore can be performed on the reflected energy 500' to produce the data signals. For example, the two polarization states can be interfered to derive interference signals (not shown) that comprise a difference in phase between the signals comprising the two polarization states. To interfere the two polarization states of the reflected energy 500', the energy-collection system 225 can analyze the reflected energy 500' at an angle of substantially forty-five degrees (45°). Thereby, the interference signals are provided with frequencies that are substantially equal to the sum and/or the difference of the first and second preselected modulation frequencies F1, F2. Once produced, the interference signals can be provided to the processing system 300" as the data signals. It will be appreciated that any suitable one-operand and/or two-operand operation can be performed on the two polarization states of the reflected energy 500'. Illustrative two-operand operations include addition, subtraction, ratio, and/or logic operations, such as AND, OR, NAND, NOR, and/or XOR.

In the manner discussed in more detail above with reference to FIGS. 7A–B, the processing system 300" can be provided in any suitable manner and, as shown in FIG. 14A, is provided substantially in the manner described above with reference to FIG. 7B. The processing system 300" is configured to receive the data signals from the measurement system 200" and includes a data acquisition system 310", a central processing system 320", a memory system 330" and a modeling system 340". Each of the data acquisition system 310", the central processing system 320", the memory system 330" and the modeling system 340" are provided in the manner described in more detail above with regard to FIG. 7B.

The processing system 300" further includes first and second frequency generators 350, 360. The first and second frequency generators 350, 360 can comprise any suitable type of frequency generator and are configure to generate the first and second preselected modulation frequencies F1, F2, respectively. Although illustrated as being disposed within the processing system 300", the first and second frequency generators 350, 360 can be separate from the processing system 300" and, as desired, may be disposed within the measurement system 200". The first and second frequency generators 350, 360 are coupled with, and configured to provide the first and second preselected modulation frequencies F1, F2 to, the beam-formation system 215" and the data acquisition system 310".

The processing system 300" can process the interference signals and/or the data signals provided by the measurement system in the manner discussed in more detail above with reference to FIG. 7B. Preferably, the data acquisition system 310" comprises a synchronous data acquisition system and is configured to lock the interference signals and/or the data signals to any of the frequencies that correspond to the interference signals and/or the data signals. The frequencies that correspond to the interference signals and/or the data signals include the first modulation frequency F1, the second modulation frequency F2, a sum of the first and second modulation frequencies F1, F2, and a difference between the first and second preselected modulation frequencies F1, F2. Such a method for acquiring the interference signals and/or the data signals sometimes is referred to as "lock-in detection."

Although the metrology system 100" is shown and described as being in the bright field detection configuration in the manner discussed above with reference to FIG. 6B, it will be appreciated that the metrology system 100" likewise can be provided in the dark field detection configuration in the manner described in more detail above with reference to FIG. 6A. Furthermore, if the beam of incident energy 500 was not modulated in the manner described above with reference to FIG. 14B, the metrology system 100" is configured to analyze simple reflectivity data as a function of the rotation angle φ when provided in the bright field detection configuration. Likewise, when provided in the dark field detection configuration, the metrology system 100" is configured to analyze simple scattering data as a function of the rotation angle φ if the beam of incident energy 500 was not modulated.

Figure 15:
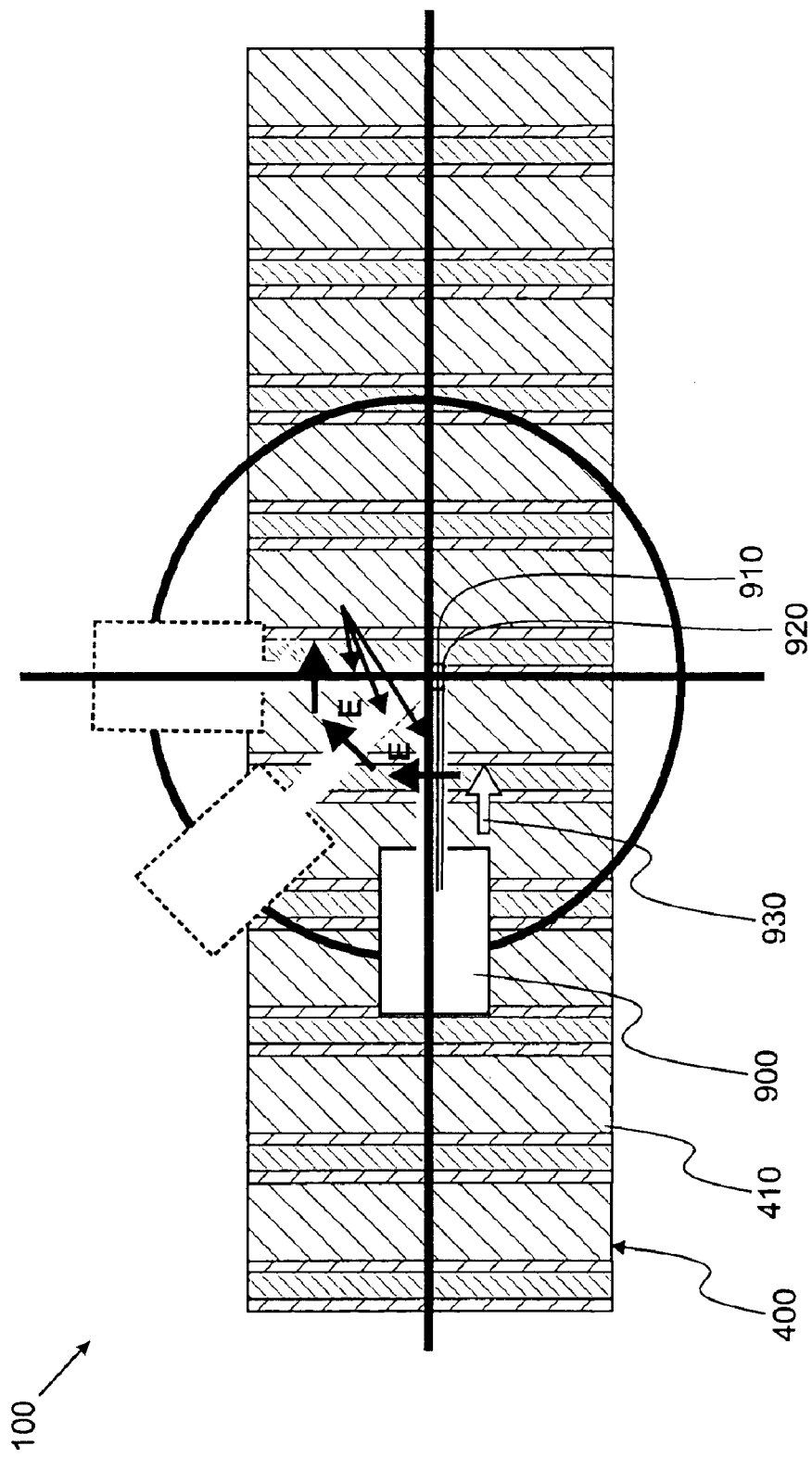
FIG. 15 illustrates another alternative embodiment of the metrology system of FIG. 2.

Radio or microwaves have a substantially long wavelength λ relative to the structures comprising the metrology system 100 and/or to any aperture or lens with reasonable size. As such, the directivity of the incident energy 500 can become lost such that the incident energy 500 appears to be coming from a point source. For this reason, the metrology system 100 can further include a near field cavity system 900 as shown in FIG. 15. An exemplary near field cavity system 900 is disclosed by Ash et al in 1974, in Nature, the disclosure of which is hereby expressly incorporated herein by reference. The near field cavity system 900 forms a microwave cavity 910 that is configured to communicate with a sub-wavelength hole (or aperture) 920 defined by the near field cavity system 900.

The near field cavity system 900 is configured to provide radiation signals 930. These radiation signals 930 preferably are evanescent and decay substantially exponentially. In operation, the metrology system 100 can detect the presence of defects in the structure 410 by measuring an input impedance (not shown) of the cavity 910. The input impedance of the cavity 910 can be readily measured. When the structure 410 includes a defect (not shown), the near field cavity system 900 can detect the defect, indicating the detection of the defect via a change in the input impedance.

When the specimen 400 is vibrated at a preselected frequency and axially relative to the axis of rotation AR, the input impedance of the cavity 910 can be modulated at the preselected frequency. The measurement system 200 and/or the energy detector 220 of the metrology system 100 can be locked on the preselected frequency. Since the direction of the electric field E outside of the cavity 900 is a function of the modes within the cavity 900. As a result, when the cavity 900 is rotated about the axis of rotation AR, a spectrum of input impedances can be obtained with respect to the rotation angle φ.

Although the various embodiments have been described with reference to optical waves and microwaves, it will be appreciated that the various embodiments apply to energy with any wavelength, such as x-rays. When the incident energy 500 comprises x-rays, for example, the angle of illumination θ should approach an angle of approximately ninety degrees (90°). If the angle of illumination θ is too large, the reflected energy 500' is approximately six orders of magnitude down. Therefore, the range of suitable angles of illumination θ comprises a range of very shallow angles when the incident energy 500 comprises x-rays. To increase the range of suitable angles of illumination θ when the incident energy 500 comprises x-rays, the beam of incident energy 500 can be modulated at a preselected frequency and synchronous detection can be performed on the incident energy in the manner described above with reference to the dark field detection configuration of the metrology system 100 shown in FIG. 6A. Thereby, a signal-to-noise ratio of the incident energy 500 can be improved for angles of illumination θ that approach approximately ninety degrees (90°) such that the range of suitable angles of illumination θ can be expanded when the incident energy 500 comprises x-rays.

The various embodiments disclosed herein are susceptible to various modifications and alternative forms, and specific examples thereof have been shown by way of example in the drawings and are herein described in detail. It should be understood, however, that the subject matter disclosed herein is not to be limited to the particular forms or methods disclosed, but to the contrary, the all modifications, equivalents, and alternatives are covered that fall within the spirit and scope of the claims.

What is claimed is:

1. An apparatus for measuring three-dimensional structures formed on a surface of a specimen, comprising:

a beam-formation system for forming a beam of incident monochromatic electromagnetic energy and for directing said beam of incident monochromatic electromagnetic energy at a predetermined illumination angle toward a preselected region on the surface of the specimen;

an energy-collection system for receiving at least a portion of said beam of incident monochromatic electromagnetic energy scattered from a three-dimensional structure formed on the surface within the preselected region and for converting said received portion of said beam of incident monochromatic electromagnetic energy into a data signal;

a rotation system for rotating said beam-formation system and said energy-collection system successively through a plurality of rotation angles about a rotation axis perpendicular to the surface of the specimen and centrally intersecting the preselected region; and a processing system for processing said data signal provided by said energy-collection system at each of said plurality of rotation angles to provide a measurement of a dimension of the three-dimensional structure.

2. The apparatus of claim 1, wherein said beam-formation system and said energy-collection system are disposed in a bright field detection configuration.

3. The apparatus of claim 1, wherein said beam-formation system and said energy-collection system are disposed in a dark field detection configuration.

4. The apparatus of claim 1, further comprising a monochromatic electromagnetic energy source for providing output energy to said beam-formation system, said beam-formation system converting said output energy into said beam of incident monochromatic electromagnetic energy.

5. The apparatus of claim 2, wherein said rotation system rotates said monochromatic electromagnetic energy source with said beam-formation system.

6. The apparatus of claim 2, wherein said monochromatic electromagnetic energy source is stationary.

7. The apparatus of claim 2, wherein said monochromatic electromagnetic energy source comprises a laser.

8. The apparatus of claim 2, wherein said beam-formation system divides said output energy into first and second energy components, polarizes said first energy component to form a P-polarized first energy component, modulates said first polarized energy components at a first modulation frequency, polarizes said second energy component to form a S-polarized second energy component, modulates said second polarized energy component at a second modulation frequency, and combines said first and second modulated, polarized energy components to form said beam of incident monochromatic electromagnetic energy.

9. The apparatus of claim 1, wherein said beam-formation system directs said beam of incident electromagnetic energy toward the preselected region with a wavelength within a predetermined range between four hundred nanometers and one hundred, fifty nanometers.

10. The apparatus of claim 9, wherein said wavelength is equal to one hundred, ninety-three nanometers.

11. The apparatus of claim 1, wherein said data signal is proportional to a phase of said received portion.

12. The apparatus of claim 1, wherein said data signal is proportional to an intensity of said received portion.

13. An apparatus for measuring three-dimensional structures formed on a surface of a specimen, comprising:

a monochromatic electromagnetic energy source for providing output energy;

a beam-formation system for converting said output energy into a beam of incident monochromatic electromagnetic energy and for directing said beam of incident monochromatic electromagnetic energy at each of a plurality of illumination angles toward a preselected region of the surface of the specimen;

an energy-collection system for receiving at least a portion of said beam of incident monochromatic electromagnetic energy scattered from a three-dimensional structure formed on the surface within the preselected region as received energy;

an energy detector for receiving reflected energy from said energy-collection system and for converting said reflected energy into data signals;

a rotation system for rotating said beam-formation system and said energy-collection system successively through a plurality of rotation angles about a rotation axis perpendicular to the surface of the specimen and centrally intersecting the preselected region; and a processing system for processing said data signals at each of said plurality of rotation angles and at each of said plurality of illumination angles to provide a measurement of a dimension of the three-dimensional structure.

14. The apparatus of claim 13, wherein said beam-formation system and said energy-collection system are disposed in a bright field detection configuration.

15. The apparatus of claim 13, wherein said beam-formation system and said energy-collection system are disposed in a dark field detection configuration.

16. The apparatus of claim 13, wherein said rotation system rotates said monochromatic electromagnetic energy source with said beam-formation system.

17. The apparatus of claim 13, wherein said monochromatic electromagnetic energy source is stationary.

18. The apparatus of claim 13, wherein said monochromatic electromagnetic energy source comprises a laser.

19. The apparatus of claim 13, wherein said beam-formation system divides said output energy into first and second energy components, polarizes said first energy component to form a P-polarized first energy component, polarizes said second energy component to form a S-polarized second energy component, modulates said first and second polarized energy components at first and second modulation frequencies, and combines said first and second modulated, polarized energy components to form said beam of incident monochromatic electromagnetic energy.

20. The apparatus of claim 13, wherein said data signals are proportional to a phase of said received portion.

21. The apparatus of claim 13, wherein said data signals are proportional to an intensity of said received portion.

22. An apparatus for measuring three-dimensional structures formed on a surface of a specimen, comprising:

means for forming a beam of incident polychromatic electromagnetic energy having a plurality of wavelengths;

means for directing said beam of incident electromagnetic energy at a predetermined illumination angle toward a preselected region on the surface of the specimen;

means for receiving at least a portion of said beam of incident electromagnetic energy scattered from a three-dimensional structure formed on the surface within the preselected region;

means for converting said received portion of said beam of incident electromagnetic energy into a data signal for each of said plurality of wavelengths;

means for rotating said directing means and said receiving means successively through a plurality of rotation angles about a rotation axis perpendicular to the surface of the specimen and centrally intersecting the preselected region; and means for processing said data signal for each of said plurality of wavelengths at each of said plurality of rotation angles to provide a measurement of a dimension of the three-dimensional structure.

23. The apparatus of claim 22, wherein said directing means and said receiving means are disposed in a bright field detection configuration.

24. The apparatus of claim 22, wherein said directing means and said receiving means are disposed in a dark field detection configuration.

25. The apparatus of claim 22, further comprising a means for providing polychromatic electromagnetic energy to said forming means, said forming means converting said polychromatic electromagnetic energy into said beam of incident polychromatic electromagnetic energy.

26. The apparatus of claim 25, wherein said rotating means rotates said providing means with said forming means.

27. The apparatus of claim 25, wherein said providing means is stationary.

28. The apparatus of claim 22, wherein said data signal is proportional to a phase of said received portion.

29. The apparatus of claim 22, wherein said data signal is proportional to an intensity of said received portion.

30. An apparatus for measuring three-dimensional structures formed on a surface of a specimen, comprising:
- a beam-formation system for forming a beam of incident electromagnetic energy and for directing said beam of incident electromagnetic energy toward a preselected region of the surface of the specimen;
- a first energy-collection system for receiving at least a portion of said beam of incident electromagnetic energy scattered from a three-dimensional structure formed on the surface within the preselected region and for converting said received portion of said beam of incident electromagnetic energy into a first data signal;
- a rotation system for rotating said beam-formation system and said first energy-collection system successively through a plurality of rotation angles about a rotation axis perpendicular to the surface of the specimen and centrally intersecting the preselected region; and
- a processing system for processing said first data signal provided by said first energy-collection system at each of said plurality of rotation angles to provide a measurement of a dimension of the three-dimensional structure.

31. The apparatus of claim 30, wherein said beam-formation system and said first energy-collection system are disposed in a bright field detection configuration.

32. The apparatus of claim 30, wherein said beam-formation system and said first energy-collection system are disposed in a dark field detection configuration.

33. The apparatus of claim 30, further comprising an electromagnetic energy source for providing output energy to said beam-formation system, said beam-formation system converting said output energy into said beam of incident monochromatic electromagnetic energy.

34. The apparatus of claim 33, wherein said rotation system rotates said electromagnetic energy source with said beam-formation system.

35. The apparatus of claim 33, wherein said electromagnetic energy source is stationary.

36. The apparatus of claim 33, wherein said electromagnetic energy source comprises a monochromatic light source.

37. The apparatus of claim 33, wherein said beam-formation system divides said output energy into first and second energy components, polarizes said first and second energy components to form P-polarized and S-polarized energy components, modulates said first and second energy components at first and second modulation frequencies, and combines said first and second modulated, polarized energy components to form said beam of incident electromagnetic energy.

38. The apparatus of claim 30, wherein said first data signal is proportional to a phase of said received portion.

39. The apparatus of claim 30, wherein said first data signal is proportional to an intensity of said received portion.

40. The apparatus of claim 30, further comprising a second energy-collection system for receiving at least a second portion of said beam of incident electromagnetic energy scattered from the three-dimensional structure and for converting said second received portion of said beam of incident electromagnetic energy into a second data signal, said second energy-collection system being rotated by said rotation system through said plurality of rotation angles about said rotation axis and being disposed in a dark field detection configuration with said beam-formation system, said processing system processing said first and second data signal at each of said plurality of rotation angles to provide the measurement of the dimension of the three-dimensional structure.

41. A system for measuring three-dimensional structures, comprising:
- a specimen having a surface that forms a plurality of three-dimensional structures;
- a polychromatic electromagnetic energy source for providing output energy;
- a beam-formation system for converting said output energy into a beam of incident polychromatic electromagnetic energy having a plurality of wavelengths and for directing said beam of incident electromagnetic energy at each of a plurality of illumination angles toward a preselected region of said surface of said specimen;
- an energy-collection system for receiving at least a portion of said beam of incident electromagnetic energy scattered from a three-dimensional structure formed on said surface within said preselected region and for converting said received portion of said beam of incident electromagnetic energy into data signals for each of said plurality of wavelengths;
- a rotation system for rotating said beam-formation system and said energy-collection system successively through a plurality of rotation angles about a rotation axis perpendicular to said surface of said specimen and centrally intersecting said preselected region; and
- a processing system for processing said data signals for each of said plurality of wavelengths at each of said plurality of rotation angles to provide a measurement of a dimension of said three-dimensional structure.

42. The system of claim 41, wherein said beam-formation system and said energy-collection system are disposed in a bright field detection configuration.

43. The system of claim 41, wherein said beam-formation system and said energy-collection system are disposed in a dark field detection configuration.

44. The system of claim 41, wherein said rotation system rotates said polychromatic electromagnetic energy source with said beam-formation system.

45. The system of claim 41, wherein said polychromatic electromagnetic energy source is stationary.

46. The system of claim 41, wherein said data signals are proportional to a phase of said received portion.

47. The system of claim 41, wherein said data signals are proportional to an intensity of said received portion.

48. The system of claim 41, wherein said measurement comprises a measurement of a sidewall angle of the three-dimensional structure.

49. The system of claim 41, wherein said measurement comprises a measurement of a height of the three-dimensional structure.

50. The system of claim 41, wherein said specimen comprises a semiconductor wafer.

51. The system of claim 50, wherein said three-dimensional structure is formed from a metallic material.

52. The system of claim 50, wherein said three-dimensional structure is formed from a dielectric material.

53. The system of claim 50, wherein said three-dimensional structure is formed from metallic and dielectric materials.

54. The system of claim 50, wherein said three-dimensional structure comprises an interconnect formed on said semiconductor wafer.

55. The system of claim 50, wherein said three-dimensional structure comprises a Copper Damascene structure formed on said semiconductor wafer.

56. The system of claim 41, wherein said processing system further processes said data signals to provide a determination of whether the specimen includes a defect.

57. The system of claim 56, wherein said defect includes an incorrect film thickness.

58. A method for measuring three-dimensional structures, comprising:
   providing a specimen;
   selecting a region on a surface of said specimen;
   forming a beam of incident electromagnetic energy;
   directing said beam of incident electromagnetic energy at an illumination angle toward said selected region;
   rotating said beam of incident electromagnetic energy successively through a plurality of rotation angles about a rotation axis perpendicular to said surface of said specimen and centrally intersecting said selected region;
   receiving at least a portion of said beam of incident electromagnetic energy scattered from a three-dimensional structure formed on said surface within said selected region at each of said plurality of rotation angles;
   converting said received portion of said beam of incident electromagnetic energy at each of said plurality of rotation angles into data signals; and
   processing said data signals to provide a measurement of a dimension of said three-dimensional structure.

59. The method of claim 58, wherein said forming said beam of incident electromagnetic energy comprises forming a beam of incident monochromatic electromagnetic energy.

60. The method of claim 58, wherein said forming said beam of incident electromagnetic energy comprises forming a beam of incident polychromatic electromagnetic energy.

61. The method of claim 58, wherein said forming said beam of incident electromagnetic energy includes converting incoming electromagnetic energy into said beam of incident electromagnetic energy.

62. The method of claim 61, wherein said converting said incoming electromagnetic energy comprises converting incoming monochromatic electromagnetic energy into said beam of incident electromagnetic energy.

63. The method of claim 61, wherein said converting said incoming electromagnetic energy comprises converting incoming polychromatic electromagnetic energy into said beam of incident electromagnetic energy.

64. The method of claim 61, wherein said converting said incoming electromagnetic energy comprises converting said incoming electromagnetic energy from a stationary source into said beam of incident electromagnetic energy.

65. The method of claim 61, wherein said forming said beam of incident electromagnetic energy includes dividing said incoming electromagnetic energy into first and second energy components, polarizing said first and second energy components to form P-polarized and S-polarized energy components, modulating said first and second energy components at first and second modulation frequencies, and combining said first and second modulated, polarized energy components to form said beam of incident electromagnetic energy.

66. The method of claim 58, wherein said receiving said received portion of said beam of incident electromagnetic energy includes receiving a specular reflection of said beam of incident electromagnetic energy reflected from said three-dimensional structure.

67. The method of claim 58, wherein said receiving said received portion of said beam of incident electromagnetic energy includes receiving a non-specular scattering of said beam of incident electromagnetic energy scattered from said three-dimensional structure.

68. The method of claim 58, wherein said converting said received portion comprises converting said received portion into data signals that are proportional to a phase of said received portion.

69. The method of claim 58, wherein said converting said received portion comprises converting said received portion into data signals that are proportional to an intensity of said received portion.

70. The method of claim 58, further comprising determining whether said specimen includes a defect.

71. An apparatus for measuring three-dimensional structures formed on a surface of a specimen, comprising:
   a plurality of beam-formation systems being disposed in a first plane parallel to the surface of the specimen and at a first plurality of preselected angles about a central preselected region of the surface, each of said plurality of beam formation systems forming a beam of incident electromagnetic energy and successively directing each of said beams of incident electromagnetic energy at a predetermined illumination angle toward said preselected region of the surface of the specimen;
   a plurality of energy-collection systems for receiving at least a portion of said successive beams of incident electromagnetic energy scattered from a three-dimensional structure formed on the surface within the preselected region and for converting said received portion of said successive beams of incident electromagnetic energy into data signals, said plurality of energy-collection systems being disposed in a second plane parallel to the surface and at a second plurality of preselected angles about the central preselected region; and
   a processing system for processing said data signal at each of said second plurality of preselected angles to provide a measurement of a dimension of the three-dimensional structure.

72. The apparatus of claim 71, wherein at least one of said plurality of beam-formation systems comprises a beam-formation system for providing a beam of incident monochromatic electromagnetic energy.

73. The apparatus of claim 71, wherein at least one of said plurality of beam-formation systems comprises a beam-formation system for providing a beam of incident polychromatic electromagnetic energy.

74. The apparatus of claim 71, wherein said plurality of beam-formation systems and said plurality of energy-collection systems are disposed in the same plane, and wherein said first plurality of preselected angles and said second plurality of preselected angles are equal.

75. The apparatus of claim 71, further comprising at least one electromagnetic energy source for providing output energy to said plurality of beam-formation systems, each of said plurality of beam-formation systems converting said output energy into said beam of incident electromagnetic energy.

76. The apparatus of claim 75, wherein each of said plurality of beam-formation systems receives said output energy from a different one of said at least one electromagnetic energy source.

77. The apparatus of claim 75, wherein at least one of said at least one electromagnetic energy source comprises a polychromatic energy source.

78. The apparatus of claim 71, at least one selected energy-collection system receives said received portion of said beam of incident electromagnetic energy from a selected one of said plurality of beam-formation systems.

79. The apparatus of claim 78, wherein at least one of said at least one selected energy-collection system and said selected beam-formation system are disposed in a bright field detection configuration.

80. The apparatus of claim 78, wherein at least one of said at least one selected energy-collection system and said selected beam-formation system are disposed in a dark field detection configuration.

81. The apparatus of claim 71, said data signals are proportional to a phase of said received portion.

82. The apparatus of claim 71, wherein said data signals are proportional to an intensity of said received portion.

* * * * *